(12) United States Patent
Rosenthal et al.

(10) Patent No.: US 10,980,631 B2
(45) Date of Patent: *Apr. 20, 2021

(54) NASAL IMPLANTS AND SYSTEMS AND METHOD OF USE

(71) Applicant: Spirox, Inc., Menlo Park, CA (US)

(72) Inventors: Michael H. Rosenthal, San Carlos, CA (US); Scott J. Baron, Menlo Park, CA (US); Donald A. Gonzales, Austin, TX (US); Iyad S. Saidi, Dunn Loring, VA (US)

(73) Assignee: Spirox, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/459,177

(22) Filed: Jul. 1, 2019

(65) Prior Publication Data
US 2019/0321164 A1    Oct. 24, 2019

Related U.S. Application Data

(62) Division of application No. 14/836,841, filed on Aug. 26, 2015, now Pat. No. 10,398,545.
(Continued)

(51) Int. Cl.
*A61B 17/34* (2006.01)
*A61F 2/18* (2006.01)
*A61F 5/56* (2006.01)

(52) U.S. Cl.
CPC .......... *A61F 2/186* (2013.01); *A61B 17/3468* (2013.01); *A61F 5/56* (2013.01);
(Continued)

(58) Field of Classification Search
CPC .... A61F 5/56; A61F 2/186; A61F 2210/0004; A61F 2210/0014; A61F 6/144;
(Continued)

(56) References Cited

U.S. PATENT DOCUMENTS 2,173,848 A    9/1939 Kraus
3,395,709 A    8/1968 Rubin
(Continued)

FOREIGN PATENT DOCUMENTS

EP    1216013    6/2006
EP    1857078    11/2007
(Continued)

OTHER PUBLICATIONS

Kim et al. "Analysis of Cartilage-Polydioxanone Foil Composte Grafts". Facial Plast Surg. Dec. 2013; 29(6): 502-505. doi:10.1055/s-0033-1360593.
(Continued)

*Primary Examiner* — Brian E Pellegrino
(74) *Attorney, Agent, or Firm* — McDonnell Boehnen Hulbert & Berghoff LLP

(57) ABSTRACT

Described are implants for placing in a body, tools for delivering the implants, and systems and methods for using implants and tools for placing in a body and more particularly to nasal implants, tools for delivering nasal implants, and systems and methods for using such implants and tools. A tool may include a hand-held implant delivery device that holds, moves, orients, inserts, or shapes an implant. An implant may be a biodegradable, longitudinal implant that may be oriented for implantation by an implant delivery device.

20 Claims, 17 Drawing Sheets

Related U.S. Application Data

(60) Provisional application No. 62/042,209, filed on Aug. 26, 2014.

(52) U.S. Cl.
CPC .............. *A61F 2210/0004* (2013.01); *A61F 2210/0014* (2013.01); *A61F 2210/0076* (2013.01); *A61F 2220/0016* (2013.01); *A61F 2230/006* (2013.01); *A61F 2250/003* (2013.01); *A61F 2250/0018* (2013.01); *A61F 2250/0025* (2013.01); *A61F 2250/0026* (2013.01); *A61F 2250/0029* (2013.01); *A61F 2250/0039* (2013.01); *A61F 2250/0098* (2013.01)

(58) Field of Classification Search
CPC ......... A61F 2250/0026; A61B 17/3468; A61B 2017/0427
See application file for complete search history.

(56) References Cited

U.S. PATENT DOCUMENTS

| | | | |
|---|---|---|---|
| 3,716,058 A | 2/1973 | Tanner, Jr. | |
| 4,265,246 A | 5/1981 | Barry | |
| 4,461,281 A | 7/1984 | Carson | |
| 4,645,491 A | 2/1987 | Evans | |
| 4,938,234 A | 7/1990 | Capriotti | |
| 5,131,382 A | 7/1992 | Meyer | |
| 5,163,952 A | 11/1992 | Froix | |
| 5,261,916 A | 11/1993 | Engelson | |
| 5,286,254 A | 2/1994 | Shapland et al. | |
| 5,342,348 A | 8/1994 | Kaplan | |
| 5,356,431 A | 10/1994 | Pierce | |
| 5,358,522 A | 10/1994 | Montgomery et al. | |
| 5,411,550 A | 5/1995 | Herweck et al. | |
| 5,419,760 A | 5/1995 | Narciso | |
| 5,464,450 A | 11/1995 | Buscemi et al. | |
| 5,500,013 A | 3/1996 | Buscemi et al. | |
| 5,531,744 A | 7/1996 | Nardella et al. | |
| 5,533,440 A | 7/1996 | Sher | |
| 5,545,208 A | 8/1996 | Wolff et al. | |
| 5,551,954 A | 9/1996 | Buscemi et al. | |
| 5,591,227 A | 1/1997 | Dinh et al. | |
| 5,637,113 A | 6/1997 | Tartaglia et al. | |
| 5,649,977 A | 7/1997 | Campbell | |
| 5,679,400 A | 10/1997 | Tuch | |
| 5,683,448 A | 11/1997 | Cragg | |
| 5,730,744 A | 3/1998 | Justin et al. | |
| 5,735,811 A | 4/1998 | Brisken | |
| 5,749,893 A | 5/1998 | Vidal et al. | |
| 5,766,237 A | 6/1998 | Cragg | |
| 5,769,883 A | 6/1998 | Buscemi et al. | |
| 5,785,647 A | 7/1998 | Tompkins et al. | |
| 5,837,008 A | 11/1998 | Berg et al. | |
| 5,843,172 A | 12/1998 | Yan | |
| 5,891,108 A | 4/1999 | Leone et al. | |
| 5,893,840 A | 4/1999 | Hull et al. | |
| 5,897,523 A | 4/1999 | Wright et al. | |
| 5,951,586 A | 9/1999 | Berg et al. | |
| 5,972,027 A | 10/1999 | Johnson | |
| 5,980,551 A | 11/1999 | Summers et al. | |
| 5,980,564 A | 11/1999 | Stinson | |
| 5,980,566 A | 11/1999 | Alt et al. | |
| 6,010,054 A | 1/2000 | Johnson et al. | |
| 6,063,101 A | 5/2000 | Jacobsen et al. | |
| 6,071,305 A | 6/2000 | Brown et al. | |
| 6,099,561 A | 8/2000 | Alt | |
| 6,106,541 A | 8/2000 | Hurbis | |
| 6,165,210 A | 12/2000 | Lau et al. | |
| 6,183,433 B1 | 2/2001 | Bays | |
| 6,238,411 B1 | 5/2001 | Thorner | |
| 6,241,747 B1 | 6/2001 | Ruff | |
| 6,241,762 B1 | 6/2001 | Shanley | |
| 6,250,307 B1 | 6/2001 | Conrad et al. | |
| 6,268,405 B1 | 7/2001 | Yao et al. | |
| 6,290,673 B1 | 9/2001 | Shanley | |
| 6,293,967 B1 | 9/2001 | Shanley | |
| 6,322,590 B1 | 11/2001 | Sillers et al. | |
| 6,390,096 B1 | 5/2002 | Conrad et al. | |
| 6,401,717 B1 | 6/2002 | Conrad et al. | |
| 6,415,796 B1 | 7/2002 | Conrad et al. | |
| 6,431,174 B1 | 8/2002 | Knudson et al. | |
| 6,450,169 B1 | 9/2002 | Conrad et al. | |
| 6,454,803 B1 | 9/2002 | Romo | |
| 6,516,806 B2 | 2/2003 | Knudson et al. | |
| 6,656,195 B2 | 12/2003 | Peters et al. | |
| 6,878,165 B2 | 4/2005 | Makino | |
| 6,899,105 B2 | 5/2005 | Krueger et al. | |
| 6,978,781 B1 | 12/2005 | Jordan | |
| 6,982,359 B1 | 1/2006 | Beaudry | |
| 7,055,523 B1 | 6/2006 | Brown | |
| 7,114,495 B2 | 10/2006 | Lockwood | |
| D536,792 S | 2/2007 | Krueger et al. | |
| 7,213,599 B2 | 5/2007 | Conrad et al. | |
| 7,237,554 B2 | 7/2007 | Conrad et al. | |
| 7,322,356 B2 | 1/2008 | Critzer et al. | |
| 7,322,993 B2 | 1/2008 | Metzger et al. | |
| 7,337,781 B2 | 3/2008 | Vassallo | |
| 7,381,222 B2 | 6/2008 | Pflueger et al. | |
| 7,396,232 B2 | 7/2008 | Fromovich et al. | |
| 7,419,497 B2 | 9/2008 | Muni et al. | |
| 7,563,267 B2 | 7/2009 | Goldfarb et al. | |
| 7,666,203 B2 | 2/2010 | Chanduszko et al. | |
| 7,762,940 B2 | 7/2010 | Henderson et al. | |
| 7,780,730 B2 | 8/2010 | Saidi | |
| 7,992,566 B2 | 8/2011 | Pflueger et al. | |
| 8,104,478 B2 | 1/2012 | Pflueger et al. | |
| 8,133,276 B2 | 3/2012 | Saidi | |
| 8,167,787 B2 | 5/2012 | Gillis | |
| 8,267,962 B2 | 9/2012 | Stupak | |
| 8,409,250 B2 | 4/2013 | Schmieding et al. | |
| 8,678,008 B2 | 3/2014 | Rousseau et al. | |
| 8,784,488 B2 | 7/2014 | Saidi | |
| 8,944,990 B2 | 2/2015 | Hamel et al. | |
| 9,480,594 B2 * | 11/2016 | Saidi ................. | A61B 17/3468 |
| 2002/0019670 A1 | 2/2002 | Crawley et al. | |
| 2002/0173848 A1 | 11/2002 | Sachs | |
| 2003/0028076 A1 | 2/2003 | Kuyava et al. | |
| 2003/0149447 A1 | 8/2003 | Morency et al. | |
| 2003/0199970 A1 | 10/2003 | Shanley | |
| 2004/0098098 A1 | 5/2004 | McGuckin et al. | |
| 2005/0004417 A1 | 1/2005 | Nelson et al. | |
| 2005/0142162 A1 | 6/2005 | Hunter et al. | |
| 2005/0154412 A1 | 7/2005 | Krueger et al. | |
| 2006/0085027 A1 | 4/2006 | Santin et al. | |
| 2006/0147492 A1 | 7/2006 | Hunter et al. | |
| 2006/0184224 A1 | 8/2006 | Angel | |
| 2006/0241650 A1 | 10/2006 | Weber et al. | |
| 2006/0276817 A1 | 12/2006 | Vassallo et al. | |
| 2007/0173848 A1 | 7/2007 | Lennox et al. | |
| 2007/0219575 A1 | 9/2007 | Mejia | |
| 2007/0250118 A1 | 10/2007 | Masini | |
| 2007/0270899 A1 | 11/2007 | aWengen et al. | |
| 2007/0277831 A1 | 12/2007 | Luhrs | |
| 2007/0293946 A1 | 12/2007 | Gonzales et al. | |
| 2008/0021495 A1 | 1/2008 | Lee et al. | |
| 2008/0027480 A1 | 1/2008 | Van Der Burg et al. | |
| 2008/0066794 A1 | 3/2008 | Durfee | |
| 2008/0077240 A1 | 3/2008 | Saidi | |
| 2008/0097335 A1 | 4/2008 | Trogden et al. | |
| 2008/0167628 A1 | 7/2008 | Li et al. | |
| 2008/0208265 A1 | 8/2008 | Frazier et al. | |
| 2008/0234818 A1 | 9/2008 | Kang et al. | |
| 2008/0312688 A1 | 12/2008 | Nawrocki et al. | |
| 2009/0024133 A1 | 1/2009 | Keady et al. | |
| 2009/0024227 A1 | 1/2009 | Lesh | |
| 2009/0099577 A1 | 4/2009 | Gonzales et al. | |
| 2009/0198216 A1 | 8/2009 | Muni et al. | |
| 2009/0204130 A1 | 8/2009 | Kantsevoy et al. | |
| 2009/0274743 A1 | 11/2009 | Edelman et al. | |
| 2009/0312791 A1 | 12/2009 | Lindh, Sr. et al. | |
| 2009/0318875 A1 | 12/2009 | Friedman | |

(56) References Cited

U.S. PATENT DOCUMENTS

| | | |
|---|---|---|
| 2010/0106255 A1 | 4/2010 | Dubin |
| 2010/0174138 A1 | 7/2010 | Chang et al. |
| 2010/0280611 A1 | 11/2010 | Saidi |
| 2011/0009872 A1 | 1/2011 | Mistry et al. |
| 2011/0251634 A1 | 10/2011 | Gonzales et al. |
| 2011/0264138 A1 | 10/2011 | Avelar et al. |
| 2012/0078367 A1 | 3/2012 | Hristov et al. |
| 2012/0215307 A1 | 8/2012 | Chen et al. |
| 2012/0310280 A1 | 12/2012 | Harrington |
| 2012/0323227 A1 | 12/2012 | Wolf et al. |
| 2012/0323232 A1 | 12/2012 | Wolf et al. |
| 2013/0217958 A1 | 8/2013 | Mujwid et al. |
| 2014/0000631 A1 | 1/2014 | Gillis et al. |
| 2014/0031835 A1* | 1/2014 | Viker ............ A61B 17/3468 606/119 |
| 2014/0039619 A1 | 2/2014 | Awengen et al. |
| 2014/0188158 A1 | 7/2014 | Servell et al. |
| 2014/0243975 A1 | 8/2014 | Saidi et al. |
| 2015/0012090 A1 | 1/2015 | Saidi |
| 2015/0013687 A1 | 1/2015 | Paraschac et al. |
| 2015/0148902 A1 | 5/2015 | Komrit |
| 2016/0058556 A1 | 3/2016 | Rosenthal et al. |
| 2016/0287367 A1 | 10/2016 | Rontal |
| 2017/0027687 A1 | 2/2017 | Kang-Budialam et al. |
| 2017/0105836 A1 | 4/2017 | Baron et al. |
| 2017/0143532 A1 | 5/2017 | Gonzales et al. |

FOREIGN PATENT DOCUMENTS

| | | |
|---|---|---|
| EP | 1475056 | 10/2010 |
| EP | 1940320 | 12/2010 |
| EP | 2692313 | 2/2014 |
| WO | 2000/76493 | 12/2000 |
| WO | 2001/01957 | 1/2001 |
| WO | 2001/19301 | 3/2001 |
| WO | 2002/076354 | 10/2002 |
| WO | 2003/015664 | 2/2003 |
| WO | 2003/041612 | 5/2003 |
| WO | 2006/093533 | 9/2006 |
| WO | 2006/101610 | 9/2006 |
| WO | 2006/107957 | 10/2006 |
| WO | 2007/134215 | 11/2007 |
| WO | 2008042058 | 4/2008 |
| WO | 2009036290 | 3/2009 |
| WO | 2010/033682 | 3/2010 |
| WO | 2010/051273 | 5/2010 |
| WO | 2010/059586 | 5/2010 |
| WO | 2010/132648 | 11/2010 |
| WO | 2011/092161 | 8/2011 |
| WO | 2012/112967 | 8/2012 |
| WO | 2014/004231 | 1/2014 |
| WO | 2015/192162 | 12/2015 |

OTHER PUBLICATIONS

Supplementary European Search Report dated Feb. 5, 2018 in European Patent Application No. 15835481.1, Applicant: Spriox, Inc., (8 pages).

PCT International Search Report for PCT/US2017/068419, Applicant: SPIROX, INC., Form PCT/ISA/210 and 220, dated Apr. 26, 2018.

PCT Written Opinion of the International Search Authority for PCT/US2017/068419, Applicant: SPI ROX, I NC., Form PCT/ISA/237, dated Apr. 26, 2018 (8 pages).

Parylene Engineering; Why use parylene; retrieved from the internet (http://www.paryleneengineering.com/why_use_parylene.htm); 3 pages; on Oct. 2, 2017.

Baron et al.; U.S. Appl. No. 15/274,986 entitled "Nasal implants and systems and method of use," filed Sep. 23, 2016.

Saidi et al.; U.S. Appl. No. 15/339,220 entitled "Nasal implants and systems and methods of use," filed Oct. 31, 2016.

De Pochat et al.; The role of septal cartilage in rhinoplasty: Cadaveric analysis and assessment of graft selection; Aesthetic Surgery Journal; 31 (8); pp. 891-896; Nov. 2011.

Friedman et al.; A simplified technique for airway correction at the nasal valve area; Otolaryngol Head Neck Surg; 131(4); pp. 519-524; Oct. 2004.

Kalan et al.; Treatment of external nasal valve (alar rim) collapse with an alar strut; Journal of Laryngology and Otology; 115(10); pp. 788-791; Oct. 2001.

Karen et al.; The use of percutaneous sutures for graft fixation in rhinoplasty; Archives Facial Plastic Surgery; 5(2); pp. 193-196; Mar.-Apr. 2003.

Lambert et al.; A new method for arterial drug delivery via removable stent (abstract); JACC; 21 (2); p. 483A; Abstract No. 834-2; Feb. 1993.

Millman; Alar Batten grafting for management of collapsed nasal valve; Laryngoscope; 112(3); pp. 574-579; Mar. 2002.

Pochat et al.; The role of septal cartilage in rhinoplasty: cadaveric analysis and assessment of graft selection; Aesthetic Surgery Journal; 31 (8); pp. 891-896; Nov. 2011.

Rhee et al.; Nasal valve surgery improves disease-specific quality of life; Laryngoscope; 115(3); pp. 437-440; Mar. 2005.

Westreich et al.; Defining nasal cartilage elasticity: Biomechanical testing of the tripod theory based on a cantilevered model; Arch Facial Plast Surg; 9(4); pp. 264-270; Jul./Aug. 2007.

Cole; Biophysics of nasal air flow: A review; American Journal of Rhinology; 14(4 ); pp. 245-249; Jul./Aug. 2000.

Cole; The four components of the nasal valve; American Journal of Rhinology; 17(2); pp. 107-110; Mar./Apr. 2003.

Friedman et al.; Nasal Valve Suspension: An Improved, Simplified Technique for Nasal Valve Collapse Laryngoscope; 113(2); pp. 381-385; Jan. 2003.

Fanous et al.; Collapsed nasal-valve widening by composite grafting to the nasal floor; Journal ofOtolaryngology; 25(5); pp. 313-316; Oct. 1996.

\* cited by examiner

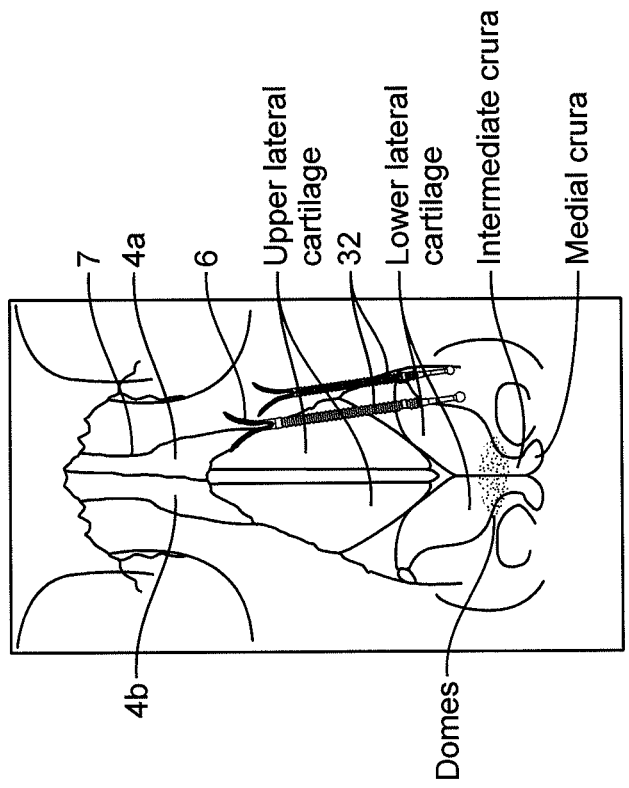
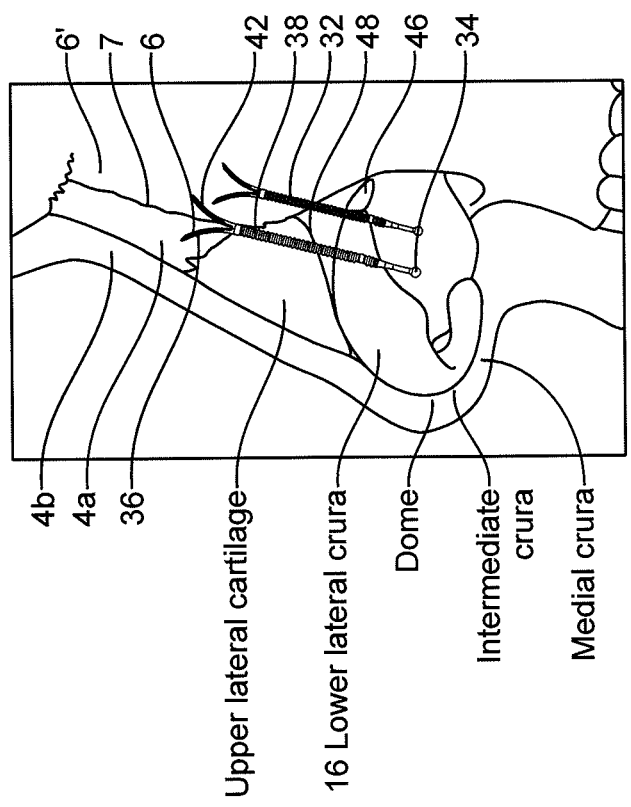
FIG. 10A
FIG. 10B

| BEAM TYPE | SLOPE AT ENDS | DEFLECTION AT ANY SECTION IN TERMS OF $x$ | MAXIMUM AND CENTER DEFLECTION |
|---|---|---|---|
| 5. Beam Simply Supported at Ends — Concentrated load $P$ at the center. | $\theta_1 = \theta_2 = \dfrac{Pl^2}{16EI}$ | $y = \dfrac{Px}{12EI}\left(\dfrac{3l^2}{4} - x^2\right)$ for $0 < x < \dfrac{l}{2}$ | $\delta_{max} = \dfrac{Pl^3}{48EI}$ |

FIG. 10C

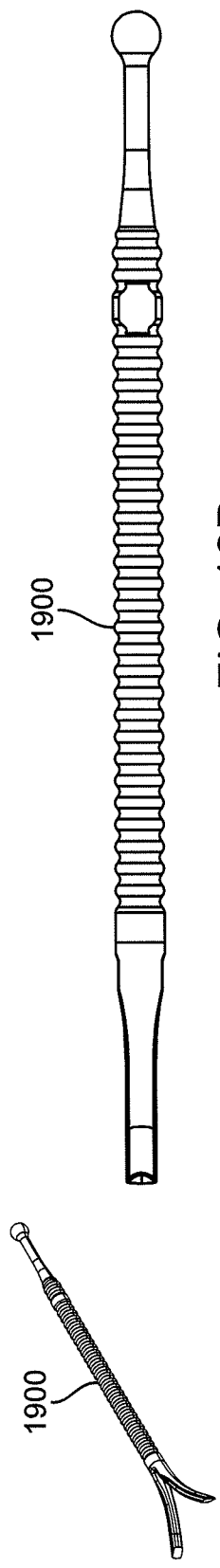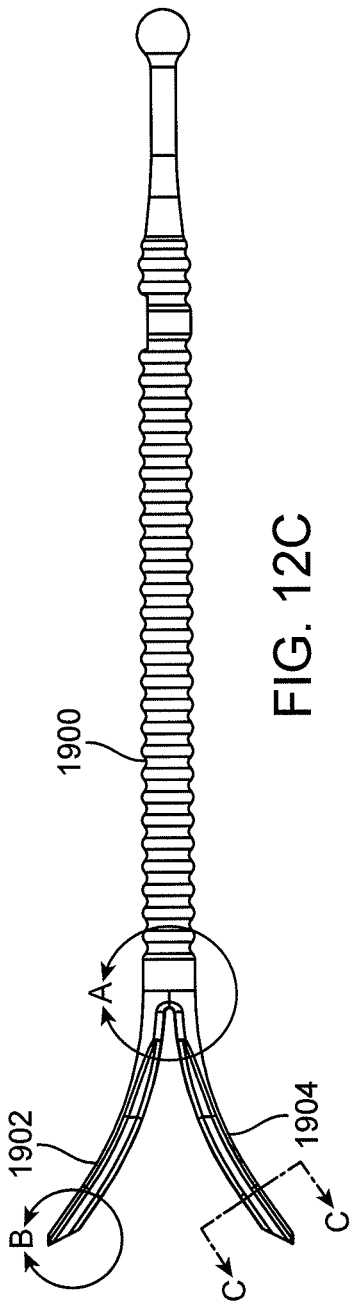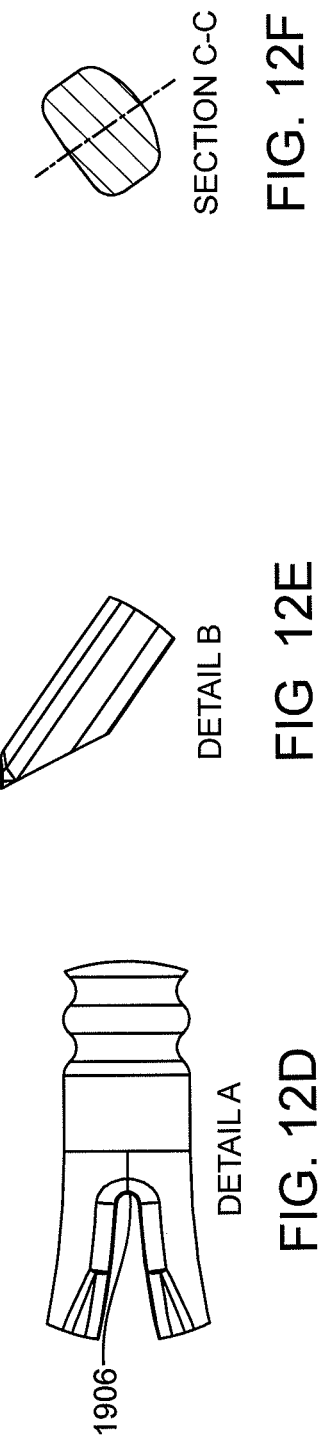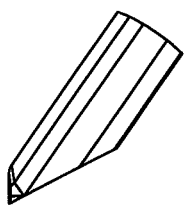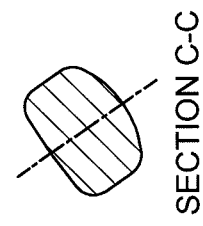

SECTION A-A

NASAL IMPLANTS AND SYSTEMS AND METHOD OF USE

CROSS REFERENCE TO RELATED APPLICATIONS

This application is a divisional of U.S. patent application Ser. No. 14/836,841, filed Aug. 26, 2015, which claims priority to U.S. Patent Application No. 62/042,209 filed Aug. 26, 2014, the disclosures of which are incorporated herein by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present invention pertains to implants for placing in a body, tools for delivering the implants, and systems and methods for using implants and tools for placing in a body and more particularly to nasal implants, tools for delivering nasal implants, and systems and methods for using such implants and tools.

BACKGROUND

The particular nasal anatomy of an individual may cause or contribute to various problems, such as cosmetic concerns, difficulty breathing, sleep apnea, or snoring, and impact an individual's health or reduce the quality of life. For example, the structure of an external or internal nasal valve may resist airflow from the nose to the lungs and prevent an individual from getting sufficient oxygen to the blood.

U.S. Pat. Nos. 8,133,276, 7,780,730, and U.S. 2012/0109298 describe implants that can be introduced into the nasal region of an individual using non-surgical injection techniques for treating a nasal valve of an individual.

There is a continued need for improvements to address problems attributed to nasal anatomy that are easier to use, last longer, are less invasive, are less expensive to manufacture, work better and so on.

SUMMARY OF THE DISCLOSURE

Described herein are implants for placing in a body, tools for delivering the implants, and systems and methods for using implants and tools for placing in a body and more particularly to nasal implants, tools for delivering nasal implants, and systems and methods for using such implants and tools. These may be useful in minimally invasive procedures, including outpatient procedures, and may result in minimal pain and rapid recovery. These systems, assemblies and methods may be used, for example, in a doctor's office or clinic, and in some cases may require only a suitable local anesthetic. These implants, assemblies, systems, and methods may be especially useful for supporting or repairing nasal tissue, such as an internal nasal valve or an external nasal valve. Some implants may provide a long-term solution for improved nasal function or nasal cosmesis: a semi-permanent implant that degrades over a long time period may provide short-term nasal tissue support while the implant is intact and may initiate a body response (e.g. a fibrotic response) that strengthens nasal tissues and provides long-term nasal tissue support. A nasal treatment system may employ a pre-shaped or shapeable nasal implant including a bioabsorbable material that provides structural support of surrounding nasal tissue. The assemblies and systems may penetrate through a patient's nasal tissue and allow precise positioning of an implant within a patient's nose.

One aspect of the invention provides a method of supporting a tissue section of a patient's nose, the method including the steps of inserting a delivery tool into tissue (e.g., mucosal, muscle, or skin tissue) of the nose; advancing an implant distally from the delivery tool to place a distal end of the implant into nasal tissue, the implant comprising a first arm at a distal end of the implant; moving the arm away from a central longitudinal axis of the implant during the advancing step; withdrawing the delivery tool to dispose a central portion of the implant in a position deep to patient's skin; and supporting the tissue section with the implant.

In some embodiments, the implant includes a second arm, the method further including moving the second arm away from the central longitudinal axis of the implant during the advancing step. In some embodiments, the implant includes a second arm, and the method further includes moving apart the first and second arms.

In some embodiments, a central portion of the implant is disposed between nasal cartilage and the patient's skin.

In some embodiments, the step of advancing an implant distally includes advancing the implant between the patient's skin and the maxillary bone at or near a maxilla nasal bone suture line.

In some embodiments, the central portion of the implant has a flexural rigidity of 10 to 590 N-mm2; of 30 to 450 N-mm2; of 60-250 N-mm2, of 75-200 N-mm2, of 9-130 N-mm2,or of 50-130 N- mm2. In some embodiments, the implant consists essentially of bioabsorbable material. In some embodiments, the implant includes more than one type of bioabsorbable material. In some embodiments, the implant includes a bioabsorbable material and a non-bioabsorbable material.

Some embodiments include the step of loading the implant into the delivery tool. In some embodiments, the delivery tool includes a handle portion and a needle disposed distal to the handle portion, and the loading step includes loading the implant into the handle portion and advancing the implant into the needle. In some embodiments the delivery tool includes a needle, and the inserting step includes inserting a distal end of the needle into tissue (e.g., mucosal tissue) of the nose. Some embodiments include the step loading the implant into the needle. In some of these embodiments, the loading step includes loading the implant into a proximal end of the needle, the method further includes advancing the implant to the distal end of the needle prior to the inserting step. In some of these embodiments, the loading step includes loading the implant into a proximal end of the needle, and the method further includes advancing the implant to the distal end of the needle prior to the inserting step. In yet some other of these embodiments, the method includes maintaining a known orientation between the implant and the needle during the inserting step.

Another aspect of the invention provides a nasal implant including a body consisting essentially of a bioabsorbable material, the body including a distal end; a proximal end; a central portion disposed between the proximal end and the distal end, the central portion having a flexural rigidity of 10 to 590 N-mm2; of 30 to 450 N-mm2; of 60-250 N-mm2 or of 75-200 N-mm2, 50-130 N-mm2, a first arm disposed at the distal end, the first arm having a proximal end fixed to the body and a distal end not fixed to the body, the distal end of the first arm being adapted to move away from a central longitudinal axis of the body from a delivery configuration toward a deployed configuration; and a strain relief section at the proximal end.

Some embodiments include a second arm, disposed at the distal end, the second arm having a proximal end fixed to the body and a distal end not fixed to the body, the distal end of the second arm being adapted to move away from a central longitudinal axis of the body from a delivery configuration toward a deployed configuration. In some of these embodiments, the first and second arms are biased toward their deployed configuration. In some of these embodiments, the first and second arms each comprise a bevel on a radially inward surface of its distal end. In some embodiments, the first and second arms each includes a bevel on a radially outward surface of its distal end.

In some embodiments, the central portion includes a plurality of sections wherein two sections have different cross-sectional areas. In some embodiments, the central portion includes ridges. In some embodiments, the implant includes a blunt proximal end.

Another aspect of the invention provides a nasal implant delivery tool including a handle; a needle extending distally from the handle, the needle having a lumen with a non-circular cross-section and a sharp distal end; and an actuator adapted to move a nasal implant along the needle lumen and out of an opening at the distal end of the needle.

In some embodiments, the delivery tool further includes an implant loading chamber communicating with the needle lumen and adapted to load the nasal implant into the needle lumen. In some embodiments, the implant loading chamber is adapted to move the nasal implant from a deployed configuration to a delivery configuration as the nasal implant is advanced into the needle lumen. In some such embodiments, the implant loading chamber is adapted to move the nasal implant from a deployed configuration to a delivery configuration as the nasal implant is advanced into the needle lumen.

Some embodiments include an actuator register adapted to indicate a position of the actuator at which the nasal implant is at the distal end of the needle lumen. In some such embodiments, the actuator register includes a marking on the actuator or on the handle.

Some embodiments include an actuator register adapted to indicate a position of the actuator at which at least a distal portion of the implant has been moved out of the needle lumen. In some such embodiments, the actuator register is a stop element preventing further movement of the actuator.

Another aspect of the invention provides a system including a delivery tool, the delivery tool including: a handle; a needle extending distally from the handle, the needle having a lumen with a non-circular cross-section having a major axis and a minor axis and a sharp distal end; and an actuator adapted to move a nasal implant along the needle lumen and out of an opening at the distal end of the needle; the system further including a nasal implant disposed in the needle lumen and including first and second arms at a distal end of the implant, the first and second arms each having a proximal end fixed to the implant and a distal end not fixed to the implant, the distal end of each arm being biased to move away from a central longitudinal axis of the implant from a delivery configuration within the needle lumen toward a deployed configuration outside of the needle lumen, the first and second arms each comprising a beveled surface engaged with an inner surface of the needle lumen on opposite ends of the major axis.

In some embodiments, the system includes a second arm at the distal end of the implant, the second arm having a proximal end fixed to the implant and a distal end not fixed to the implant, the distal end of the second arm being biased to move away from a central longitudinal axis of the implant from a delivery configuration within the needle lumen toward a deployed configuration outside of the needle lumen, the second arm including a beveled surface engaged with an inner surface of the needle lumen on an opposite end of the major axis from the first arm.

In some embodiments, the delivery tool further includes an implant loading chamber communicating with the needle lumen and adapted to load the nasal implant into the needle lumen. In some such embodiments, the implant loading chamber is adapted to move the nasal implant from the deployed configuration to the delivery configuration as the nasal implant is advanced into the needle lumen.

In some embodiments, the delivery tool further includes an actuator register adapted to indicate a position of the actuator at which the nasal implant is at the distal end of the needle lumen. In some such embodiments, the actuator register comprises a marking (or markings) on the actuator or on the handle.

In some embodiments, the delivery tool further includes an actuator register adapted to indicate a position of the actuator at which at least a distal portion of the implant has been moved out of the needle lumen. In some such embodiments, the actuator register is a stop element preventing further movement of the actuator. In some embodiments, the delivery tool includes an indicator configured to provide a signal that an implant (e.g., a distal portion of an implant) has been moved out the needle lumen.

In some embodiments, the first and second arms of the nasal implant each include a bevel on a radially inward surface of its distal end. In some embodiments, the nasal implant further includes a strain relief section at the proximal end. In some embodiments, the nasal implant further includes a central portion disposed between the proximal end and the distal end, the central portion having a flexural rigidity of 50-130 N-mm2. In some embodiments, the nasal implant consists essentially of biodegradable material.

In general, in one embodiment, a nasal implant including a body including a distal end; a proximal end; a central portion disposed between the proximal end and the distal end, the central portion having a flexural rigidity of about 9-130 N-mm2; and a first arm disposed at the distal end, the arm having a proximal end fixed to the body and a distal end not fixed to the body, the distal end of the arm being adapted to move away from a central longitudinal axis of the body from a delivery configuration toward a deployed configuration.

This and other embodiments can include one or more of the following features. The body can consist essentially of a bioabsorbable material. At least one portion of the implant can be composed of a bioabsorbable material. The implant can include two or more different bioabsorbable materials. The first arm and a portion of the central portion can include a first bioabsorbable material having a first bioabsorption profile, the proximal end can include a second bioabsorbable material having a second bioabsorption profile, the second bioabsorption profile can be shorter than the first bioabsorption profile. The implant can further include one or more strain relief sections within the implant. The flexural rigidity of the central portion can be less than about 130 N-mm2. At least two portions of the implant can have a different flexural rigidity value. The implant can further include a portion composed of a non-absorbable material. At least one of the distal end, proximal end, or central portion can be composed of a core made of a non-absorbable or an absorbable material and an outer layer made of a different non-absorbable or absorbable material from the core. The core and outer layer can be fixedly laminated to one another. The core and outer layer can be slid-ably engaged with one another. The implant can further include a second arm having a proximal end fixed to the body and a distal end not fixed to the body, the distal end of the second arm can be adapted to move away from a central longitudinal axis of the body from a delivery configuration toward a deployed configuration. The first and second arms can be biased toward their deployed configuration. The first and second arms each can include a bevel on a radially inward surface of its distal end. The first and second arms each can include a bevel on a radially outward surface of its distal end. The central portion can include multiple sections wherein the sections have different cross-sectional areas. The central portion can include a plurality of small projections. The implant can further include a blunt proximal end. The first and second arms can be configured to self-expand toward the deployed configuration. The flexural rigidity of the central portion can be about 50 to 130 N-mm2.

In general, in one embodiment, a method of supporting a tissue section of a patient's nose, the method including inserting a delivery tool into tissue of the nose; advancing an implant distally from the delivery tool to place a distal end of the implant within the nasal tissue, the implant including a first arm at a distal end of the implant; the first arm moving away from a central longitudinal axis of the implant during the advancing step; withdrawing the delivery tool to dispose a central portion of the implant within the nasal tissue, the central portion of the implant having a flexural rigidity of about 9 to 130 N-mm2; and supporting the tissue section with the implant.

This and other embodiments can include one or more of the following features. The implant can include a second arm, the method can further include the second arm moving away from the central longitudinal axis of the implant during the advancing step. Advancing the implant can include retracting a portion of the delivery tool to allow the first arm and second arm to self-expand to move away from the central longitudinal axis of the implant. Advancing the implant can include pushing the implant distally such that the first arm and second arm each engage the tissue thereby moving away from the central longitudinal axis of the implant. Advancing the implant can include pushing the implant distally and retracting a portion of the delivery tool such that the first arm and second arm each engage the tissue thereby moving away from the central longitudinal axis of the implant. Advancing the implant can include the first arm forming a first arm incision path, the first arm incision path can have a longitudinal axis that can be offset from a longitudinal axis of the delivery tool. Advancing the implant can include the second arm forming a second arm incision path, the second arm incision path can have a longitudinal axis that can be offset from a longitudinal axis of the delivery tool. The first arm incision path and second arm incision path can form an angle that is less than 180 degrees. Advancing can include the first arm and second arm each engaging a portion of tissue located between the first arm and the second arm. The flexural rigidity of the central portion can be about 50 to 130 N-mm2. The implant can consist essentially of bioabsorbable material. The implant can include more than one bioabsorbable material. The implant can include a bioabsorbable material and a non-absorbable material. The method can further include loading the implant into the delivery tool. The delivery tool can include a handle portion and a needle disposed distal to the handle portion, the loading step can include loading the implant into the handle portion and advancing the implant into the needle. The delivery tool can include a needle, the inserting step can include inserting a distal end of the needle into tissue of the nose. The method can further include loading the implant into the needle. The loading step can include loading the implant into a proximal end of the needle, the method can further include advancing the implant to the distal end of the needle prior to the inserting step. The loading step can include collapsing the first arm of the implant prior to entering the proximal end of the needle. The loading step can include collapsing the first arm and second arm of the implant prior to entering the proximal end of the needle. The method can further include maintaining a known orientation between the implant and the needle during the inserting step. Maintaining the known orientation between the implant and the needle can include engaging the implant with a portion of a lumen of the needle having a non-circular cross section.

In general, in one embodiment, a nasal implant delivery tool including a handle; a needle extending distally from the handle, the needle having a lumen with a portion of the lumen having a non-circular cross-section, the needle having a sharp distal end; and an actuator adapted to move a nasal implant along the needle lumen and out of an opening at the distal end of the needle.

This and other embodiments can include one or more of the following features. The needle can include a low friction coating on an external surface of the needle. The needle can include substantially banded markings at various positions along the needle. The delivery tool can further include an implant loading chamber communicating with the needle lumen and adapted to load the nasal implant into the needle lumen. The implant loading chamber can be adapted to move the nasal implant from a deployed configuration to a delivery configuration as the nasal implant is advanced into the needle lumen. The delivery tool can further include an actuator register adapted to indicate a position of the actuator at which the nasal implant can be at the distal end of the needle lumen. The actuator register can include a marking on the actuator or on the handle. The delivery tool can further include an actuator register adapted to indicate a position of the actuator at which at least a distal portion of the implant has been moved out of the needle lumen. The actuator register can be a stop element preventing further movement of the actuator.

In general, in one embodiment, a system including a delivery tool, the delivery tool including a handle; a needle extending distally from the handle, the needle having a lumen with a portion of the needle having a non-circular cross-section, the needle having a major axis and a minor axis and a sharp distal end; and an actuator adapted to move a nasal implant along the needle lumen and out of an opening at the distal end of the needle; the system can further include a nasal implant disposed in the needle lumen and including a first arm at a distal end of the implant, the arm having a proximal end fixed to the implant and a distal end not fixed to the implant, the distal end of the arm being biased to move away from a central longitudinal axis of the implant from a delivery configuration within the needle lumen toward a deployed configuration outside of the needle lumen.

This and other embodiments can include one or more of the following features. The system can further include a second arm at the distal end of the implant, the second arm can have a proximal end fixed to the implant and a distal end not fixed to the implant, the distal end of the second arm can be biased to move away from a central longitudinal axis of the implant from a delivery configuration within the needle lumen toward a deployed configuration outside of the needle lumen. The first arm can include a beveled surface engaged with an inner surface of the needle lumen on an end of the major axis. The second arm can include a beveled surface engaged with an inner surface of the needle lumen on an opposite end of the major axis from the first arm.

The delivery tool can further include an implant loading chamber communicating with the needle lumen and adapted to load the nasal implant into the needle lumen. The implant loading chamber can be adapted to move the nasal implant from the deployed configuration to the delivery configuration as the nasal implant is advanced into the needle lumen. The delivery tool can further include an actuator register adapted to indicate a position of the actuator at which the nasal implant can be at the distal end of the needle lumen. The actuator register can include a marking on the actuator or on the handle. The delivery tool can further include an actuator register adapted to indicate a position of the actuator at which at least a distal portion of the implant can be moved out of the needle lumen. The delivery tool can include an indicator configured to provide a signal that a distal portion of the implant has been moved out of the needle lumen. The actuator register can be a stop element preventing further movement of the actuator. The first and second arms of the nasal implant each can include a bevel on a radially inward surface of its distal end. The nasal implant can further include a central portion disposed between the proximal end and the distal end, the central portion can have a flexural rigidity of about 9-130 N-mm2. The nasal implant can further include a central portion disposed between the proximal end and the distal end, the central portion can have a flexural rigidity of less than about 130 N-mm2. The nasal implant can further include a central portion disposed between the proximal end and the distal end, the central portion can have a flexural rigidity of about 50-130 N-mm2. The nasal implant can further include a strain relief section at the proximal end. The nasal implant can consist essentially of biodegradable material. The system can include a nasal implant with a first arm with a tip or an end engaged with an inner surface of the needle lumen. The nasal implant can be any of the implants of the previous embodiments.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 10A-10B show the placement of multiple implants in a patient's nose.

FIG. 10C shows a table depicting an equation for center deflection of a simply supported beam.

FIGS. 12A-12F show drawings of a molded implant with beveled ends.

DETAILED DESCRIPTION

Figure 1:
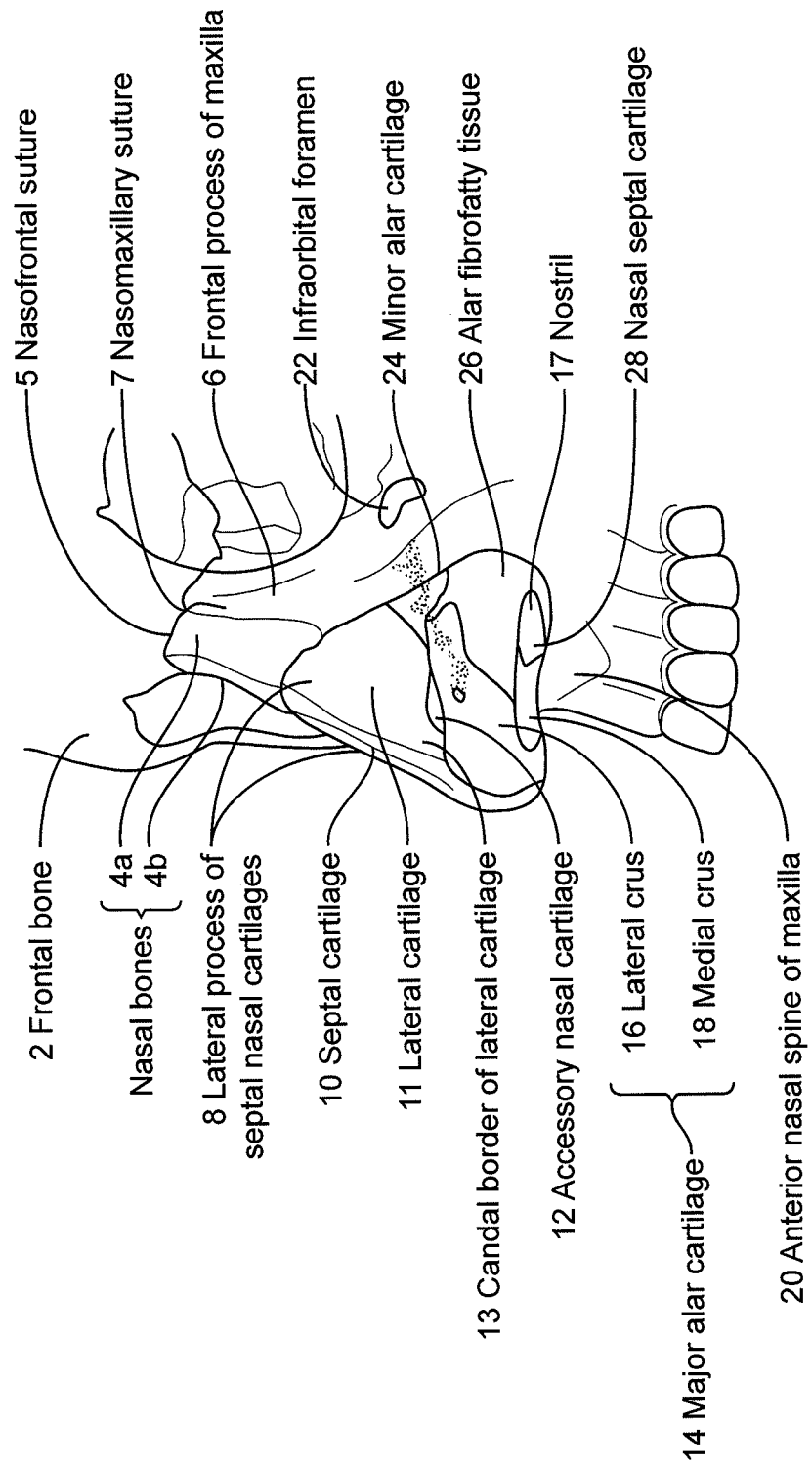
FIG. 1 shows the underlying structural anatomy and tissues of a nose on a face without overlying skin or tissue.

Described herein are implants, devices, systems and methods using implants, devices and systems for altering, enhancing, repairing, and supporting a body tissue. Such systems and methods may be used to support or change any tissue in the body, but may be especially beneficial for use in nasal tissue in a patient's nose, such as to aid breathing or change the cosmetic appearance of the nose. A system as described herein generally includes an implant to be placed into a patient's body, an implant delivery tool to deliver the implant to the patient and an actuator adapted to move the nasal implant through the delivery tool, although the system components may instead be used separately from one another. An implant delivery tool may include a handle and a piercing end (a needle) for piercing a body tissue. An implant may be sufficiently strong to provide support to a tissue or to change a tissue shape when the implant is in place in the body. An implant may also be sufficiently flexible to change shape during implant delivery or allow tissue to move when the implant is in place in the body. An implant delivery tool may be a handheld delivery tool and may be configured to place an implant relatively close to the surface of the body, such as under or in cartilage or other connective tissue, muscle or skin. An implant delivery tool may have a small piercing end (needle) for making a small, relatively unobtrusive opening through a surface of the body (such as through skin, mucous, or epithelium) and moving through underlying tissues to deliver an implant to the patient. An implant delivery tool may deliver the implant to the tissue through the opening in the body in a minimally invasive way and may cause only minimal scarring. In addition to minimizing pain, infection, and swelling, such a minimally invasive system and methods described herein may also make unnecessary the use of large bandages to cover the opening in the skin and tissues after implant delivery which can otherwise cause patient discomfort or bring unwanted attention. This may especially be important if the patient receives an implant in a highly visible location, such as receiving a nasal implant in a nose and the bandage is on the person's face. In some cases implant delivery may be very fast, taking only seconds or minutes to perform. A system and method as described herein may be very safe and generally does not require a surgical procedure. In addition to being performed in a hospital, it can generally also be performed in a doctor's office or outpatient facility or another care facility outside a hospital. A delivery tool for delivering an implant into a patient's body may make a small hole that easily heals by using a relatively small needle (similar in size to a needle used for drawing blood or placing an IV (intravenous) line into a patient) for placing the implant in the body.

An implant may be placed near the skin's surface or may be placed deeply into a body tissue. An implant may be shaped to have a low profile in at least one dimension (e.g., height) so that it can lie relatively flatly against tissue when implanted. In the case of a nasal implant placed near the surface of a patient's nose, an implant may have such a low profile that the presence of the implant is not obvious from looking at the patient.

An implant may be able to take on different configurations or different shapes, such as having a delivery configuration during implant delivery, a deployment configuration when fully deployed, and other configurations before, during, or after delivery or deployment. An implant may have a contracted configuration and an expanded configuration. An implant may be contracted or configured to contract to fit in an implant delivery tool and fit through a small placement hole made by the delivery tool. An implant may be configured to expand in a body tissue when placed in a patient to carry out its supporting or tissue shaping function. An expanded implant may better support or alter a body structure or tissue or may help hold an implant in place. An implant may have an implant body and a projection, and the projection may be able to move independently or relative to the implant body. A projection may move from an outward position towards the central longitudinal axis of the implant, contracting the overall profile of the implant so that an implant with a relatively larger cross-sectional profile can fit (temporarily) into a relatively smaller region of a delivery device before the implant takes on an expanded configuration in the body tissue. An end may be forked and two or more implant projections (e.g., arms on the end of the fork) may also move towards each other and together contract the overall implant profile or may diverge (e.g., move away from each other) and expand the overall implant profile. An implant may include an elastomeric or other flexible material so that the implant body or projections (arms) can change shape without breaking. An implant or a portion of an implant such as an arm may have a curvilinear or arc shape over part or all of the implant or implant portion. An implant, especially an implant projection (arm) may include one or more features, such as bevels, that may be useful for guiding the implant into an implant delivery tool or for guiding the implant into a tissue. A bevel may be on an end of a projection.

Implants, devices, systems and methods as described herein may be used in any body tissue, but may be especially useful for supporting or altering a nasal internal valve or other nasal tissue. The internal nasal valve is a complex 3-dimensional structure that controls respiration and how air (oxygen) enters into and exits from the body. Dysfunction in the internal nasal valve has a dramatic and negative effect on a person's ability to breathe.

FIG. 1 shows the underlying structural anatomy and tissues of a face. The outer layers of overlying skin and muscle have been removed to better show the underlying cartilage and bone that provide structure. The nose sits in the middle of the face and has important responsibilities in olfaction (smelling) and controlling respiration. The nose controls respiration by restricting the flow of air. The nose has two airflow pathways, one on each side of the nose (starting with each nostril) which combine to form a single airflow pathway into the body. Air from the nose flows through the trachea and into the lungs where the air is spread out in the lobules of the lungs and oxygen is absorbed for use by the entire body. Each of the two airflow pathways in the nose have several segments including two types of nasal valves (called external nasal valves and internal nasal valves) along each nasal airflow pathway that act to control airflow through the nose and so together the external and internal valves control airflow into and out of the body. The amount of airflow resistance caused by the valves needs to be "just right"; either too much or too little resistance causes breathing and other problems. The valves are tissues that surround the airflow and the amount of resistance they provide to the airflow is determined largely by their shape and their size (their internal cross-sectional area). The internal nasal valve on each pathway is the narrowest segment of the pathway in the nose and generally creates most of the resistance. Besides the important function of controlling airflow, the internal nasal valves also help give the nose its distinctive shape. A nasal valve is shaped and supported by various structures in the nose and face, with upper lateral cartilage playing a significant role in its form and function. Large and even small changes in internal nasal valve structure can impair nasal breathing, as well as change the cosmetic appearance of the nose. These changes generally act to reduce the cross-sectional area of the internal valve, and can be caused by surgery, another medical treatment, or trauma to the face. Additionally, there are variations of nasal valve structure between individuals, with some individuals having significantly narrowed valves due to weakened or misshaped cartilage, commonly observed as a pinched nose. A narrowed valve region increases the acceleration of airflow and simultaneously decreases intraluminal pressure, causing the valves to collapse. While even normal nasal valves can collapse under great respiratory pressures, dysfunctional internal valves can collapse even during normal breathing, with reduced oxygen flow, snoring and mouth breathing as undesirable consequences.

The nose includes the external nose that protrudes from the face and a nasal cavity underneath the external nose. From top to bottom, the external nose has a root, a bridge, a dorsum (ridge), a free tip (apex), and a columella. The external nose is appended to the piriform aperture, the continuous free edges of the pear shaped opening of the nasal cavity in the skull and is formed by the nasal bones and the maxilla. As shown in FIG. 1, the nose sits in the middle of the face, framed by the bones of the head, with frontal bone 2 superior to the nose, lateral maxilla frontal process 6 lateral to it, and the maxilla anterior nasal spine 20 inferior to it. (Another lateral maxilla frontal process on the other side of the nose is not visible in this view). The external nose can be roughly divided into three layers from outside to inside: an overlying skin and muscle layer (removed in this view), a middle cartilage and bony framework layer, and an inner mucosal layer (not readily visible in this view).

While the middle cartilage and bony framework layer provides form, structure, and support to the nose, it is also organized to allow the nose to be flexible and wiggle and bend in different directions. It can also be roughly divided into three sections: from top to bottom, they are an upper (superior) bony third, and middle and lower (inferior) cartilaginous thirds. The upper third includes paired left nasal bone 4a and right nasal bone 4b that are joined in the middle of the nose and form the top (or superior) part of the bridge of the nose. Nasal bone 4a (along with lateral maxilla frontal process 6) joins frontal bone 2 superiorly to form the nasofrontal (nasion) suture line 5. Laterally, nasal bone 4a joins the maxilla at its frontal process 6 to form a fibrous joint at the maxilla nasal bone suture line 7 (or nasomaxillary suture line). The middle third of the cartilage and bony framework layer includes septal cartilage 10 which forms part of the septum of the nose and internally separates the nostrils and the two airflow pathways. Lateral process 8 of septal cartilage 10 merges superiorly with upper lateral cartilage 11. (Another lateral process on the other side of the nose that merges with upper lateral cartilage on the other side of the nose is not visible in this view). FIG. 1 also shows minor alar cartilage 24, one of several accessory cartilages which provide support and allow movement of the nose, and which impact the complex 3-dimensional shape of the nose. Upper lateral cartilage 11 is normally fairly stiff and it has much of the responsibility for supporting the side of the nose. In conjunction with septal cartilage tissue, it helps to form the internal nasal valve, which is inside the nose under the upper lateral cartilage and not readily visible in this view. As mentioned above, there are two internal nasal valves (one on either side of the nose). Each internal nasal valve is formed by and bordered medially by septal cartilage 10, laterally by the caudal margin 13 of the upper lateral cartilage, and inferiorly by the head of inferior turbinate (not visible in this view) and surrounds an opening through which air flows. The attachment of the upper lateral cartilage to the septum (septal cartilage) forms an angle that defines the internal nasal valve angle (also called simply "valve angle"). The internal nasal valve angle is the narrowest part of the nasal airway and creates resistance that controls airflow through it. There is some natural variation between individuals in their nasal valve angles, and valve angles may change over time as a natural consequence of aging. Valve angle is determined in part by genetics, and an ethnic group has a particular average valve angle associated with it. There is also variation in valve angles between individuals, even within a particular ethnic group, and between an individual's left and right valves. Nasal valve angles may also be altered as a result of surgery, trauma or another intervention. A valve with a valve angle of less than about 10 degrees may generally be considered collapsed, causing nasal airway obstruction with nasal sidewall collapse upon inspiration and may merit treatment such as described herein. A valve angle that is greater 10 degrees may also cause some airway obstruction, cosmetic concern or another concern and may also merit treatment but its dysfunction is generally not as severe as a collapsed valve. Valves in need of treatment may be candidates for treatment using the implants, devices, systems and methods described herein.

The lower third of the cartilage and bony framework layer includes major alar cartilage (also referred to as lower lateral cartilage or inferior lateral cartilage, based on its location and to distinguish it from upper lateral cartilage) that help shape the nostrils and the tip of the nose. This cartilage is softer and more mobile than upper lateral cartilage, and it allows the tip of the nose to move. Major alar cartilage 14 is U shaped and includes lateral crus 16 and medial crus 18. Major alar cartilage 14 forms part of external valve around nostril 17 (also called nares), though it does not quite reach the bone laterally. The lower third of the cartilage and bony framework layer also includes alar fibrofatty tissue 26 of alar that fills the gap between lateral crus 16 and the bone. FIG. 1 also shows small accessory alar cartilage 12 that links the major alar and lateral cartilage 8 of the cartilage and bony framework layer.

Figure 2A:
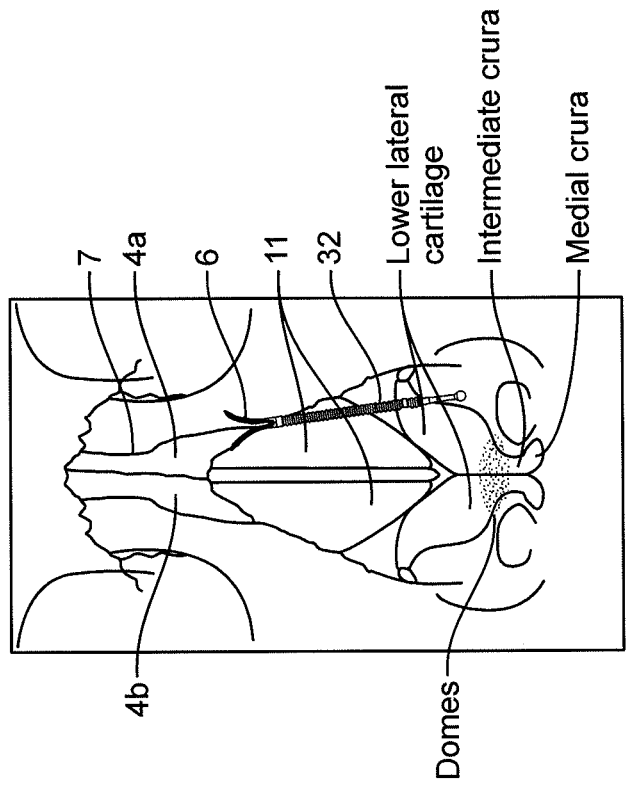
FIGS. 2A-2B show placement of an implant in a patient's nose.
Figure 2B:
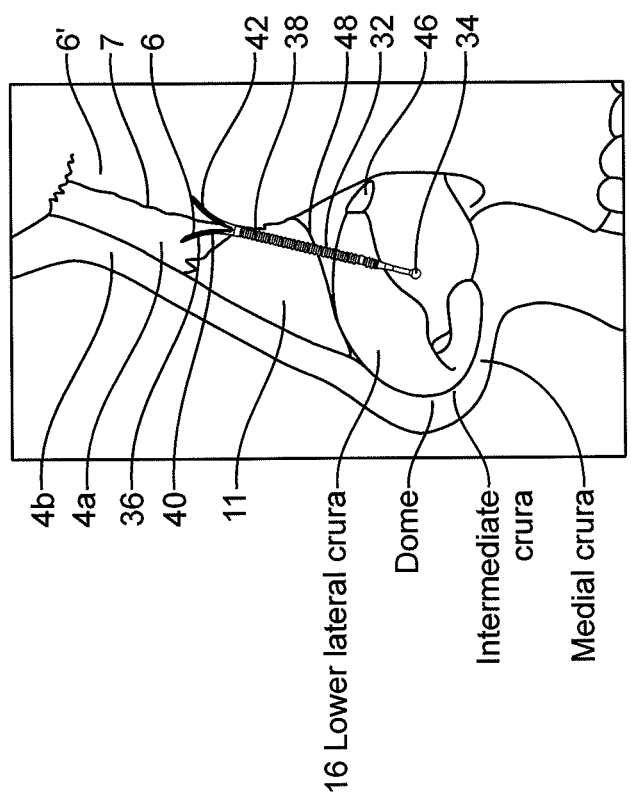

As mentioned above, the nose is a complex, 3-dimensional structure. It may be desirable to change its shape or better support its structure in order to improve or maintain its function or appearance (cosmesis), but it can difficult to change one aspect of the nose without adversely affecting another part. Indeed, previous surgical interventions are one cause of altered nasal valve function that may be treated using the systems and methods described herein. Described herein are implants, devices, systems and methods function for changing or supporting an aspect of a body structure or shape, including of the nose. FIGS. 2A and 2B show front and side views, respectively, of an implant 32 implanted in a patient's nose and supporting a tissue section of a patient's nose. Implant 32 may be useful for maintaining or improving nasal function or appearance. Implant 32 is underlying the skin and muscles which have been removed to better illustrate the implant and the underlying nasal structures and implant. FIGS. 2A-2B show implant 32 in place for supporting or changing an internal nasal valve. Implant 32 apposes structures in the cartilage and bony framework layer under the skin and muscle. Implant 32 has a body with proximal end 34, distal end 36 and central portion 38 between the proximal and distal ends. Central portion 38 is in a position between the nasal cartilage and patient skin or muscle. Central portion 38 apposes upper lateral cartilage 11 and lower lateral crus 16 of the lower lateral cartilage. As mentioned above, along with the septal cartilage, the caudal end of the upper lateral cartilage defines the internal valve angle, and central portion 38 of implant 32 also apposes the caudal end 48 of the upper lateral cartilage 11 and so overlies or acts on the internal valve wall, providing support to or changing a shape of the internal valve. Distal end 36 of implant 32 apposes structures in the upper part of cartilage and bony framework. In these examples in FIGS. 2A-2B, distal end 36 of implant 32 is forked with first arm 40 and second arm 42 forming the tines of the fork. Each arm has a proximal end fixed to the implant body and a distal end not fixed to the body. In this example, the arms apposes nasal bone 4a, frontal process 6 of the maxilla bone, and maxilla nasal bone suture line 7 (nasomaxillary suture line). In some variations, a distal end of an implant may be apposed or in proximity to one of more structures in the upper layer or any of the structures or tissues in the middle or lower cartilage and bony framework layer (e.g., accessory cartilage, major alar cartilage, minor alar cartilage, septal cartilage, maxilla, etc.).

A method of supporting a tissue section of a patient's nose may include the steps of inserting a delivery tool into mucosal tissue of the nose; advancing an implant distally from the delivery tool to place a distal end of the implant into nasal tissue, the implant comprising first and second arms at a distal end of the implant; moving apart the first and second arms of the implant during the advancing step; withdrawing the delivery tool to dispose a central portion of the implant in a position between nasal cartilage and the patient's skin; and supporting the tissue section with the implant.

When in place in a body tissue, such as in a nasal tissue or any other type of tissue in the body, a bone or other structure may provide cantilever support to an implant. For example, extending an implant for supporting a nasal valve beyond the start of the maxillary bone may provide cantilever support. Implant 32 may leverage one or more forces between the different portions of the implant to provide a force to alter or support a tissue in need of alteration or support. Implant 32 may leverage force from one or more underlying structures (e.g., a bony structure such as a maxillary or nasal bone, an accessory, upper, or lower cartilage) to a structure needing support (e.g., an accessory, upper, or lower cartilage such as a caudal region of an upper lateral cartilage). Linking an upper cartilage and lower cartilage will support or strengthen the internal nasal valve and improve nasal appearance or breathing or reduce snoring or other problems. As discussed above, upper lateral cartilage 11, in particular its caudal margin, along with the dorsal cartilage of the dorsal septum, and the inferior turbinates, borders the internal nasal valve. Implant 32 acts to support or alter the internal valve. In a particular example, a force may be leveraged by the implant to alter or support a caudal (lower) region of an upper lateral cartilage and thereby alter or support an internal nasal valve and internal valve angle. A valve angle may be increased, decreased or may stay the same in response but in general will stay the same or be increased. Although the overlying skin and tissue of the nose have been removed in this figure, they may provide force and may hold the implant against the underlying tissues anywhere along its length, such as holding the implant over the maxillary or nasal bone, or over its entire length. Nasal bone 4 may exert a force on implant 32. An implant may behave as a lever to provide support to a structure. A structure such as a bone (e.g., a nasal or facial bone), cartilage, or other body structure may place a force on an implant to thereby provide support along the length of an implant and provide support to a body structure, such as a nasal valve. For example, a nasal or maxillary bone may provide force to upper lateral cartilage 8 and lower lateral cartilage 16.

In some variations, an implant is a biocompatible implant useful for nasal valve repair. An implant may be used to strengthen a nasal valve in a patient's nose. An implant may support the cartilage and help resist or reduce movement of the cartilage during inhalation, thereby keeping the patient's airway open. While implant 32 in FIGS. 2A-2B is apposing or in proximity to particular structures in the cartilage and bony framework layer of a patient's nose, as well as to the overlying muscle/skin, an entire implant or one or more regions of an implant may be apposed to or placed in proximity to any (body) cavity, structure, or tissue in a patient's body. For example, a projection (arm) or other protrusion, or part of an arm or other protrusion, a central region, part of a central region, a distal end, a proximal end, a strain relief portion, a feature, a ridge, etc. may be apposed to or placed in proximity to any (body) cavity, structure, or tissue in a patient's body. In some variations, an implant or a region of an implant may be apposed to or placed in proximity to one or more of any cavity, structure or tissue, such as a facial or nasal bone, cartilage, connective tissue, fascia, fat, respiratory epithelium, squamous epithelium, squamous epithelium of the nasal cavity, ligament, muscle, mucous, skin, (alar) fibrofatty tissue, a blood vessel, mucosa, nasal mucosa, a frontal bone, a lacrimal bone, a maxilla bone (e.g., an anterior nasal spine, a frontal process), a nasal bone, a vomer bone, a nasomaxillary suture, a nasofrontal suture, an accessory nasal cartilage, an upper lateral cartilage (including a cranial border, a caudal border or a central region of the upper lateral cartilage), a lower lateral cartilage, a major alar cartilage (e.g., lateral crus, medial crus), a minor cartilage, a septal cartilage (e.g., a lateral process, nasal septal cartilage), etc. An implant may be apposed to or placed in proximity to one or more other implants or synthetic structures. An implant apposed to or in proximity to a (body) cavity, structure, or tissue may act upon it (e.g., support it, place a force on it or resist a force from it, act as a fulcrum for a force from it, etc.) or may not act upon it. For example, part of an implant may lie across a tissue, but not have a substantial interaction or impact on that tissue. An implant may be placed overlying or underlying one or more of the above mentioned tissues. An implant may be placed in any orientation relative to these tissues and may lie substantially parallel, perpendicular or skewed relative to a long or short axis of a cavity, a structure, a tissue or another implant. In some examples, an implant is placed within a nasal tissue. In some embodiments, an implant is located partially within a nasal tissue and partially within a surrounding tissue (e.g., a maxilla). An implant may be attached (e.g., with an adhesive, a suture, a screw, etc.) to a structure, a tissue, or another implant (such as those described herein) or may lie close or in contact with a structure, a tissue, or another implant (such as those described herein). An implant may be placed so that a proximal tip of the implant has sufficient clearance from the nostril rim for insertion through mucosal tissue. An implant may be held in place by a force between the implant and a structure, a tissue, or another implant such as a compressive force. An implant may be held (at least partially) in place by forces on the implant from an overlying layer. In some particular examples, a distal end of a nasal implant is held (at least partially held) in place against the maxilla and/or nasal bones and/or nasomaxillary suture by (the tightness of) the overlying skin and muscle pressing the implant against the bone or suture.

Figure 3A:
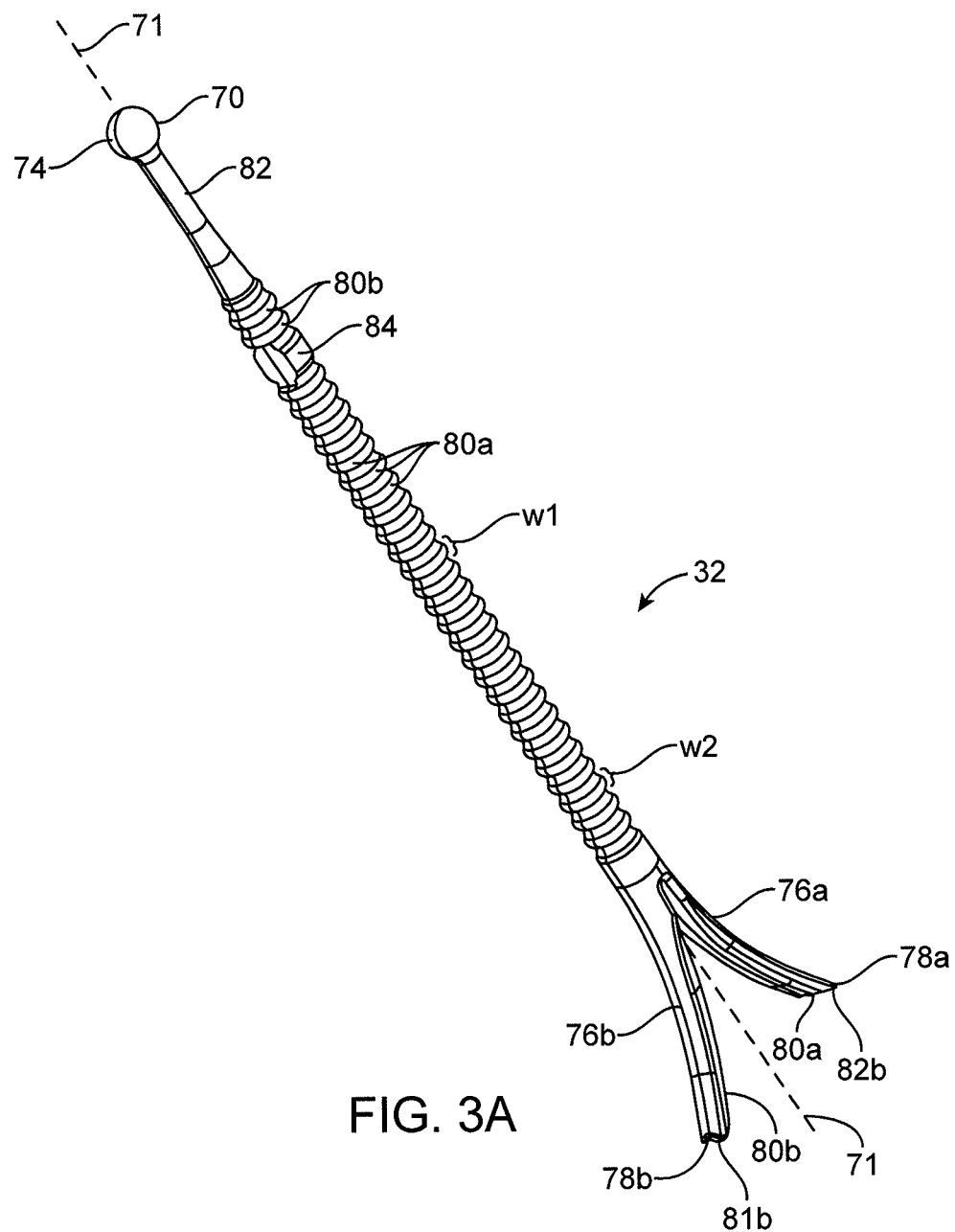
FIGS. 3A-3B shows an implant with arms and bevels at the ends of the arms.

FIG. 3A shows an implant for acting on a body tissue with a generally longitudinal body having first end 70, second end 72, and a central portion disposed between the first end and the second end. The implant defines a central longitudinal axis 71. In some examples, the first end of the implant is in a proximal location of an insertion site in a tissue. Second (or distal) end 70 of implant 32 has first arm 76a and second arm 76b, each arm having a proximal end fixed to the body and a distal end not fixed to the body.

In some variations, an implant is adapted to have or take on different configurations. For example, an implant may have a contracted configuration and an expanded configuration. An implant may be able to take on a (continuous) range of configurations in between the contracted and expanded configurations. In some cases, an implant may be able to be held in any of these configurations. A contracted configuration may be a delivery configuration and may be useful for delivering an implant, such as moving the implant through an implant delivery device and placing it into a body tissue. A contracted implant may be small enough to readily fit into a relatively small delivery device. An implant in an expanded configuration may be a deployed configuration and may be useful, for example, for holding the implant in the body tissue once the implant is in place in the body. An expanded configuration may also or instead aid in bioabsorption of a bioabsorbable implant, such as by providing access of body fluids involved with bioabsorption to the implant. A range of configurations in between the delivery and deployed configurations may, for example, aid in guiding the implant to a desired location during deployment.

In some variations, an arm of an implant may be adapted to move relative to the implant body. An arm may be adapted to move away from, move around, or move towards a central axis of the implant body. An arm or a portion of an arm may include a material that is adapted to move the arm from a first position to a second position. A material to move the arm may, for example, be a resiliently deformable material or a shape memory material. An arm may be biased to move to a second position.

Two or more arms may be adapted such that they can be moved (e.g., pushed or pulled) towards or away from one another without breaking or cracking. An arm may be sufficiently movable (e.g., deformable, flexible, etc.) to travel up to 10°, up to 20°, up to 30°, up to 40°, up to 45°, up to 50°, up to 60°, up to 70°, up to 80°, up to 90°, up to 145° or up to 180° relative to a central longitudinal axis of the implant body from a first position to a second position without breaking or cracking, or may travel between any of the these ranges (e.g., travel from 30° up to 70°, from 10° up to 50°, etc.) In some examples, an arm in a first position on an implant may be oriented parallel (or close to parallel) to a central longitudinal axis of an implant and then may be moved to a second position so that the arm is obliquely oriented (e.g., as described above, up to 10°, up to 20°, etc.) with respect to its first position and the central axis of the implant body.

In some examples, the implant has first and second arms, and the distal ends of the arms are adapted to move away from a central longitudinal axis of the body. The first and second arms may move from a delivery configuration toward a deployed configuration, or from a contracted to an expanded configuration. In some examples, the first and second arms are biased towards their deployed configuration. In some examples, the biased arms may move from a delivery configuration toward a deployed configuration when a force from a delivery device is removed, such as by removing the implant from the device.

Arms on an implant, such as first and second arms 76a and 76b, may have different shapes or different configurations, or they may have the same shape or same configuration. The arms may be mirror images of each other. Instead of, or in addition to distal arms, a distal end may have protrusions. An arm or protrusion may be useful for carrying out an implant or implant arm function, and they may work alone, with one another, or with another structure in order to carry out the function(s). Such functions may include, for example, guiding the implant in a delivery tool, orienting the implant in a delivery tool, orienting the implant relative to an actuator (pushrod), a delivery tool, or patient tissue, holding the implant in a delivery tool, orienting the implant with respect to the patient, cutting or enabling arm travel through patient tissue, compressing or moving patient tissue, holding the implant in the patient tissue, placing a force on the patient tissue, and so on. An arm or protrusion may be or may have a barb, a bump, a cilia or cilia-like, a generally elongated rod, a hair, a hook, a loop, a prong, a rod, a spike, a thread, a tine, etc. An arm or protrusion may be relatively rigid or may be relatively flexible. An arm or protrusion may be more flexible or more rigid than another part or all of the rest of an implant. An arm or protrusion may place a force on another part of an implant, on another implant or on a body tissue. An arm or protrusion may provide or cause friction (e.g., static friction) between an arm or protrusion and another part of an implant, on another implant or on a body tissue. An implant may have one or more than one arm, projection or protrusion such 2, 3, 4, 5, 6, more than 6, more than 10, more than 20, more than 100, more than 1000, etc. An arm or protrusion may be relatively flexible in a first dimension (e.g., in a depth or when extending away from a central longitudinal axis of the implant and relatively less flexible or inflexible in a second axis (e.g., along a width or from side to side or along a length). An arm may be configured to be able to be drawn or pushed inward (e.g., towards a central longitudinal axis of the implant) and to be pushed or extended outward (e.g., away from a central longitudinal axis of the implant).

Figure 3B:
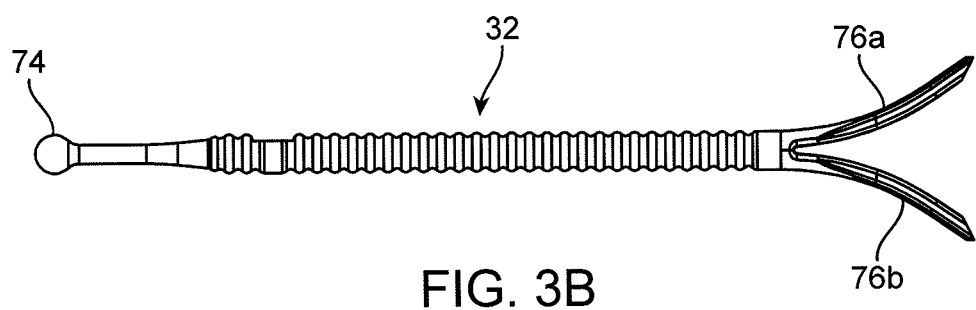

FIGS. 3A-3B also shows first arm 76a and second arm 76b having respectively, first arm inner bevel 80a and second arm inner bevel 80b, on radially inward surfaces of the distal end 72 of implant 32. A bevel (e.g., a slanted surface that meets another at any angle but 90°), especially an inner bevel, may be useful, for example, for guiding an implant or implant arm through body tissue. First arm inner bevel 80a has a first sharp edge 81a and second arm inner bevel 80b has a second sharp edge 81b. A sharp end of an inner bevel may be especially useful for cutting through tissue during implant deployment and to provide a path in body tissue for an implant arm to travel. For example, a sharp end of an inner bevel may cut or move through tissue without causing undue tearing or excessive damage. In some examples, an implant with a body and an arm, a cross-sectional area of the arm is smaller than is a cross-sectional area of the body. Generally, a small sharp cut through a tissue causes less pain and heals better than does a tissue that has been torn or subject to a larger cut. As described in more detail below, a sharp end of a bevel may cut through the tissue, and the angled end portion of the bevel and the rest of the arm may follow the sharp end as it moves through the tissue during implant deployment. The cut, slice or path through the tissue on the distal end may have a smaller cross-sectional area than does the implant body or the tissue contacting portion of an implant delivery device. Because the bevel acts to guide the arm through the tissue in front of a delivery device and the arm is smaller than the distal end of delivery device which houses the implant: the cut made by the bevel and the insertion path created by the bevel and arm may in some cases need only to be large enough for the arm to move through it; it does not need to be large enough for the delivery device or the implant body to move through. An implant with a flexible or otherwise movable arm (e.g., relative to an implant body) may be pushed or otherwise propelled through a body tissue during implant deployment, and the face (or angled portion) of an inner bevel may push against body tissue, urging the arm away from the central longitudinal axis of the implant body (and towards a deployed configuration). Instead, or additionally, an implant arm may be biased towards a deployed configuration, and the bevel may help move the biased implant arm towards a deployed configuration and deployed implant position in body tissue.

A system as described herein may include a delivery tool, the delivery tool including a handle; a needle extending distally from the handle, and an actuator adapted to move a nasal implant along the needle lumen and out of an opening at the distal end of the needle. A needle (e.g., in a delivery tool or system) may have a lumen with a non-circular cross-section having a major axis and a minor axis and a sharp distal end. The system may further include a nasal implant disposed in the needle lumen and including a first arm at a distal end of the implant, the arm having a proximal end fixed to the implant and a distal end not fixed to the implant, the distal end of the arm being biased to move away from a central longitudinal axis of the implant from a delivery configuration within the needle lumen toward a deployed configuration outside of the needle lumen, the first arm comprising a beveled surface engaged with an inner surface of the needle lumen on an end of the major axis. An implant of implant of a system may further include a second arm at the distal end of the implant, the second arm having a proximal end fixed to the implant and a distal end not fixed to the implant, the distal end of the second arm being biased to move away from a central longitudinal axis of the implant from a delivery configuration within the needle lumen toward a deployed configuration outside of the needle lumen, the second arm comprising a beveled surface engaged with an inner surface of the needle lumen on an opposite end of the major axis from the first arm.

FIG. 3A also shows first arm 76a or second arm 76b each having respectively, first arm outer bevel 78a and second arm outer bevel 78b, on radially outward surfaces of distal end 72 on implant 32. An outer bevel may be useful, for example, for guiding an implant into a delivery device, for contracting an implant into a contracted configuration, for orienting an implant in a delivery device, for guiding an implant through a delivery device, etc. Inner bevel 80a and outer bevel 78a on first arm 76a form a double bevel: the bevels or slanted surfaces share an edge (e.g., the two slanted surfaces meet each other at any angle but 90°) or may flare away from each other. In some examples, first and second or inner and outer bevels or slanted surfaces that meet another at any angle but 90° and do not share an edge (e.g., the bevels form from different edges). An implant or an arm or a protrusion may have one or more than one bevel or sloped surface or edge that meets another at any angle but 90°. A bevel may be at an end of an arm or protrusion or along a side of a projection or protrusion.

An implant, arm, or protrusion may have other or additional features such as a gripper, a prong, a tooth, etc. A feature may be angled relative to the implant, arm, or protrusion such that the feature holds the implant, arm, or protrusion in place in a delivery device or tissue. A feature on an arm or protrusion may limit or prevent substantial proximal and/or distal implant movement or side-to-side (lateral) movement. FIG. 3A shows implant 32 with a plurality of segments.

An implant may have one or more proximal end features, distal end features, or body features such as described herein or any features shown in US 2011/0251634 to Gonzales et al., US 2012/0109298 to Iyad Saidi; or U.S. patent application Ser. No. 14/192,365 filed Feb. 27, 2014. FIGS. 3A-3B shows implant 32 with proximal feature 74 at the proximal end. As shown, proximal feature 74 is a blunt end. A proximal feature may be sharp or flat, but in general will be rounded or atraumatic. An atraumatic end may prevent the proximal implant end from damaging, cutting, or exiting a tissue when it is in place in the tissue, such as in a nasal tissue. A proximal feature may help to anchor or otherwise hold an implant in place in the tissue in which it is implanted. As described in further detail below, a proximal feature may also be configured to accept or mate with a plunger or actuator to aid in orienting the implant in a delivery device or in moving the implant through a delivery device and implanting the implant into tissue. A proximal feature and an actuator or plunger may interact in any way that allows the actuator to move the implant. For example, an implant may have concave end and a plunger or actuator may have a convex end. Implant 32 also has strain relief section 82. As shown, strain relief section 82 has a relatively smaller cross-sectional area (e.g., a diameter) than another portion of the implant. A strain relief section may be larger than another area, but may provide strain relief by having a different configuration or a different material. A strain relief section may be more flexible or may have a less flexural rigidity than another region of the implant. A strain relief region may be useful to accommodate movement of a tissue, such as a nose so that the nose can bend. An implant for use in nasal or facial tissue may be configured so that the strain relief section is adjacent to mucosa to accommodate movement of the nose when the implant is in place in a nasal tissue. A strain relief section may work in conjunction with a proximal feature such as a blunt end to hold an implant in a tissue (e.g., tissue may form a collar around the neck and the proximal end may prevent movement through the collar).

Implant 32 also has a central bridging region. The central bridging region may be especially useful for bridging an area in need of support, such as weak or collapsed area between structures on either (both) ends. Such an area may be weaker or may have more force generally placed on it such that it requires more support. A central bridging region may bridge a weak or collapsed nasal valve in a nose. Support for the bridging region may be provided from the regions of the implant near the bridging region. A central region may include one or more ribs (also called ridges). Implant 32 has a plurality of ribs 80a, 80b (or ridges) which may be a central bridging region. Body features such as a rib may help anchor an implant in place, such as by catching tissue against the rib, valley, or otherwise. An implant may have one or more ribs or other body features, such as a bevel, scallop, a wing, etc. An implant may have from 0-50 body features (such as ribs), or no body features (such as ribs), 1 body features (such as ribs), 2 body features (such as ribs), 3 body features (such as ribs), 4 body features (such as ribs), 5 body features (such as ribs), from 5 body features (such as ribs) to 10 body features (such as ribs), from 10 body features (such as ribs) to 20 body features (such as ribs), from 20 body features (such as ribs) to 30 body features (such as ribs), from 30 body features (such as ribs) to 50 body features (such as ribs), etc. or any amount of body features (such as ribs) in between any of these numbers. As shown in FIG. 3A a first rib has a first rib width W1 and a second rib has a second rib width W2. Rib widths W1 and W2 may be the same size or may be different sizes. A first rib may have a first rib diameter and a second rib may have a second rib diameter. The first and second rib diameters may be the same size or may be different sizes. For example, ribs along one end, such as the distal end, may be thicker or have a large diameter to provide more leverage (e.g., against a maxilla bone), while ribs along the proximal end may be thinner or have a smaller diameter to allow more implant flexibility. In other cases, a feature along the distal end may be thinner or have a smaller diameter, for example to reduce or eliminate any undesired rib profile that may be visible on the outside surface of the nose. A feature such as a rib may be thinner and allow movement of the nose, such as during breathing (inspiration and expiration). A rib may provide a relatively larger implant surface area which may aid in speed or uniformity of biodegradation of a biodegradable implant. Ribs may aid in the flexibility of the implant; having more ribs or having larger valleys between the ribs may increase the implant flexibility.

In some variations, an implant may have a relatively low profile (e.g., short height) in at least one dimension (length, width, height). An implant height may, for example, less than 1 mm, less than 2 mm, less than 3 mm, less than 4 mm, less than 5 mm, less than 10 mm, less than 20 mm, or any size in between these, e.g., from 1 mm to 2 mm, from 1 to 5 mm, from 2 mm to 4 mm, etc. A low profile implant may be particularly beneficial, for example, because it may be inserted through a relatively small implant hole that heals easily, it may be the desired shape to fit anatomy of the space into which it is implanted, or it may not be obviously visible when implanted. An implant height may be chosen based on the implant environment and desired effect of the implant. For example, in the face and nose, underlying cartilage and bone generally determine face and nose shape, though muscle and skin play a role as well. The muscle, skin and associated tissues that cover the underlying cartilage and bone tend to take on the shape of the underlying structure that they cover. Skin and muscle thickness vary between individuals. Some people have relatively thicker skin and muscle and others have thinner skin and muscle. A relatively tall implant located over cartilage or bone may cause an obvious bump or protrusion in overlying thin muscle and skin that may be noticeable simply by looking at the person who may feel uncomfortable or self-conscious due to the attention, but may not cause an obvious bump or protrusion in a person with thicker muscle and skin which may better accommodate or mask the implant. An implant with a relatively small height may create a relatively low profile that is not obvious through the skin when the implant is in place in the nose. A low profile implant may in some cases make a small bump or protrusion that is detectable by close inspection or palpation. A body of implant may be curved or bent (and may have various features that are not straight), but in general will be relatively straight and able to bend or flex. For example, an implant may flex to a minimum bend radius of 15 mm+/−0.5 mm.

Different regions of an implant may have material properties, such as strength, flexibility, rigidity, flexural rigidity, etc. An implant may have a material property chosen to come close to a material property of a body structure. For example, a flexural rigidity of a nasal implant may be the same as or close to the flexural rigidity of nasal tissue such as cartilage. As described below, some nasal cartilage has a modulus of elasticity measured to be between 5 and 32 MPa. An implant, or a portion of an implant such as a central region, an end region, an arm region, a proximal feature, a distal feature, a protrusion, a bump, or other part of an implant as described herein may have a modulus of elasticity between 5 and 32 MPa or greater than 2, 4, 5, 10, 15, 20, 25, 30, 32, 35, 40, or 50 MPa or less than 2, 4, 5, 10, 15, 20, 25, 30, 32, 35, 40, or 50 MPa or any value in between, such as between 2 and 50 MPa, between 10 and 30 MPa, etc. A flexural rigidity of some batten grafts formed of septal cartilage has been determined to be between 50 and 130 N-mm2 or 50-140 N-mm2 and the flexural rigidity of an implant or portion of an implant may also be within this range. An implant flexural rigidity may also be greater or less than this. For example, other supporting structures in a body may work with an implant in providing additional support and a lesser amount of support is needed from the implant or supporting tissues may also be weak and greater support may be needed from the implant. An implant, or a portion of an implant such as a central region, an end region, an arm region, a proximal feature, a distal feature, a protrusion, a bump, or other part of an implant as described herein may have a flexural rigidity of greater than 10, greater than 30, greater than 50, greater than 75, greater than 100, greater than 150, greater than 200, greater than 300, greater than 400 or less than 600, less than 500, less than 420 less than 400, less than 300, less than 200, less than 130, less than 100, less than 50. For example, an implant or portion of an implant may have a flexural rigidity between 10 to 590 N-mm$^2$; of 30 to 450 N-mm$^2$; of 60-250 N-mm2; of 75-200 N-mm2; 50 and 130 N-mm2; or 9 and 130 N-mm2. In some embodiments the implant has a central portion with a flexural rigidity that is less than about 130 N-mm2. In some embodiments the implant has a central portion with a flexural rigidity that is from about 10 to about 130 N-mm2. In some embodiments the implant has a central portion with a flexural rigidity that is about 50 to 130 N-mm2. The material properties of a bioabsorbable implant change over time; thus a bioabsorbable implant be configured to have any of the material properties, such as those described above after a period of time in a body or exposure to a body fluid.

Another aspect of the invention provides an implant delivery tool for delivering an implant. An implant delivery tool may include a delivery handle and an actuator. A delivery tool may include a handle, a needle extending distally from the handle and a sharp distal end. An actuator for an implant delivery tool may be adapted to move an implant (e.g., a nasal implant) along the needle lumen and out of an opening at the distal end of the needle. In some variations, the needle may have a lumen with a non-circular cross-section. The tool may be adapted to be hand-held. The tool may be adapted to deliver an implant to a nose or face of a patient. A delivery tool may include an indicator configured to provide a signal about a status of the implant or the delivery tool. FIG. 6B shows delivery tool 400 with an implant indicator. Snap feature 406 on plunger 404 of delivery tool 400 is configured to move or snap into mating pocket 408 on handle 402 of delivery tool 400 when the plunger is advanced distally to move an implant (not shown in this view) distally. Moving or snapping the snap feature into the mating pocket may create an audible "click", "snap" or other sound. A snap feature may be locked or held in connection with the mating pocket. A mating feature may move into a mating pocket when an implant is in a particular location in the delivery tool, or when an implant is partially or fully deployed. Some examples include the step of indicating with an indicator a location of an implant (e.g., a distal location, a deployment location) etc. A mating feature may be removed or unlocked from a handle, such as by manually depressing the snap feature in the pocket of the handle. This may be useful, for example, for releasing the plunger and re-loading an additional (second, third, etc.) into the delivery tool. An indicator may provide a signal that an implant is loaded (in place in the delivery tool), that part of an implant has been moved out of the needle (e.g., that a distal portion of an implant has been moved out of the needle), or that an entire implant may be moved out of a needle. A signal may be, for example, an audio signal (e.g., a beep, a buzz, a sound, etc.; a tactile signal (such as a vibratory signal), a visual signal (such as a colored or white light, a flash or a longer duration light signal), etc.

FIGS. 4A-4D and 5A-B show different views of an implant delivery tool 300. Implant delivery tool 300 includes handle 302 and actuator 306. Handle 302 has grippable housing 308, which may be a grippable handle and needle 312. Needle 312 may have sharp distal end 314 adapted to pierce a body tissue. In some examples, a distal end of a needle may be sufficiently sharp to pierce nasal or facial tissue, such as any described herein. A sharp distal end may minimize nasal tearing. A needle may be any size, such as the size of a hypodermic needle as known in the art; e.g., outer diameter of 8 gauge, 10 gauge, 12 gauge, 14 gauge, 16 gauge, 18 gauge, 20 gauge, etc. A needle may be sized to fit between the mucosa, epithelium, muscle skin and cartilage or bone of the nose and face. In some examples, a needle may fit between a mucosa/skin and cartilage of the nose. A needle may be long enough to place an implant through tissue (e.g., at least 50 mm, at least 75 mm, at least 100 mm, at least 115 mm, at least 125 mm, or at least 150 mm. A distal end of the needle may include an opening adapted to fit an implant inside. Needle 312 has a lumen which may be adapted to house or hold an implant. The lumen may have any cross-sectional profile, such as circular, non-circular, oval or ovoid, ellipsoid, triangular, square, rectangular, hexagonal, etc. In some variations, different regions of the lumen may have different cross-sectional profiles. A lumen with a non-circular cross-section may be oriented with respect to the handle of the delivery tool, and a handle of the delivery tool may control the orientation of the lumen (and control an implant oriented in the lumen). A handle may control the orientation of the implant during implant delivery. A lumen may have 1, 2, or 2, 3, 4, 5, or more than 2, 3, 4, or 5 different cross-sectional profiles. For example, a proximal portion may be circular and a distal portion may be non-circular. In some examples, a proximal lumen region may be circular, a middle lumen region may be non-circular (e.g., oval, ovoid, ellipsoid, or any other shape including those described above), and a distal lumen region may be circular. A lumen with a non-circular cross-section may have a major axis and a minor axis. An implant may be configured to engage or may be engaged with a lumen of a needle or with a lumen of a handle. An implant disposed in the handle lumen or needle lumen may have first and second arms at a distal end of the implant, the first and second arms may each have a proximal end fixed to the implant and a distal end not fixed to the implant, the distal end of each arm may be being biased to move away from a central longitudinal axis of the implant from a delivery configuration within the needle lumen toward a deployed configuration outside of the needle lumen, the first and second arms each comprising a beveled surface (e.g., an outer beveled surface) engaged with an inner surface of the needle lumen on opposite ends of the major axis. Some examples include maintaining a known orientation between an implant and a lumen (needle) during the inserting step.

Figure 4A:
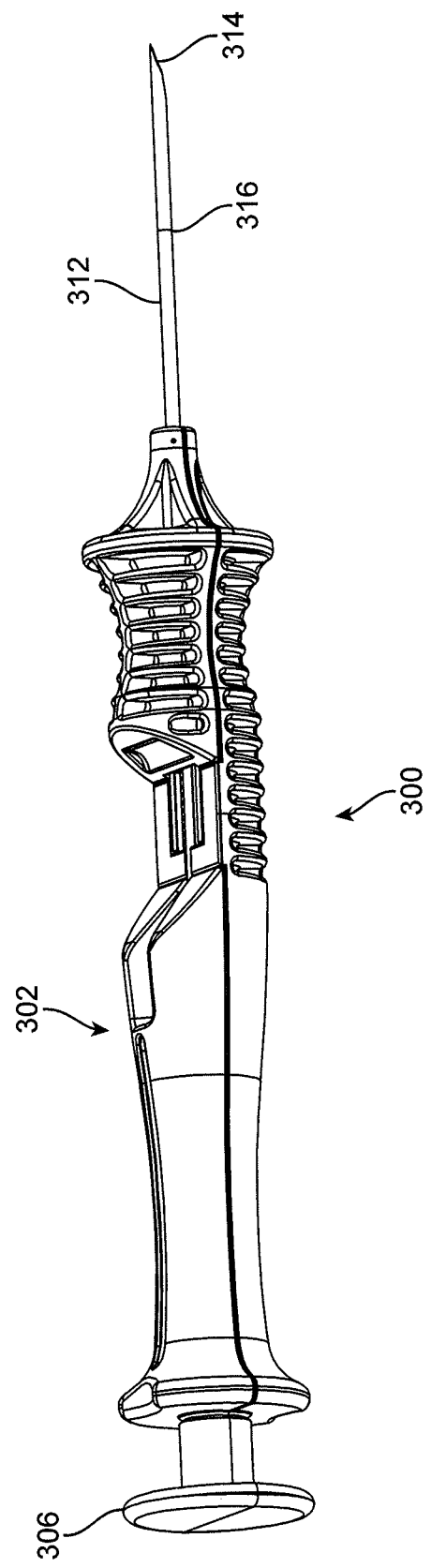
FIGS. 4A-4B show an implant delivery device for placing an implant into a body tissue.
Figure 4B:
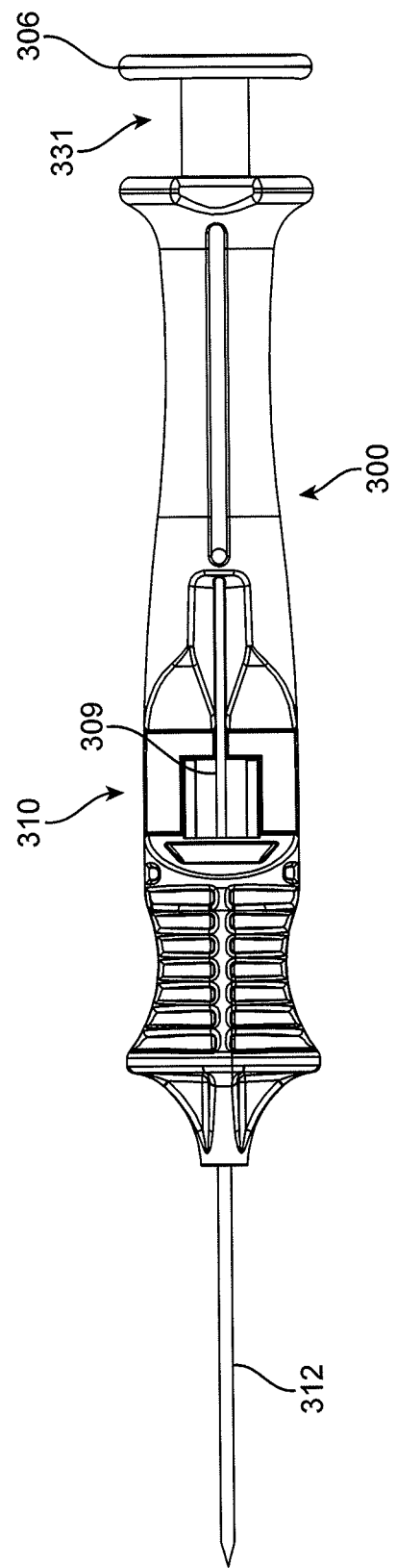
Figure 4C:
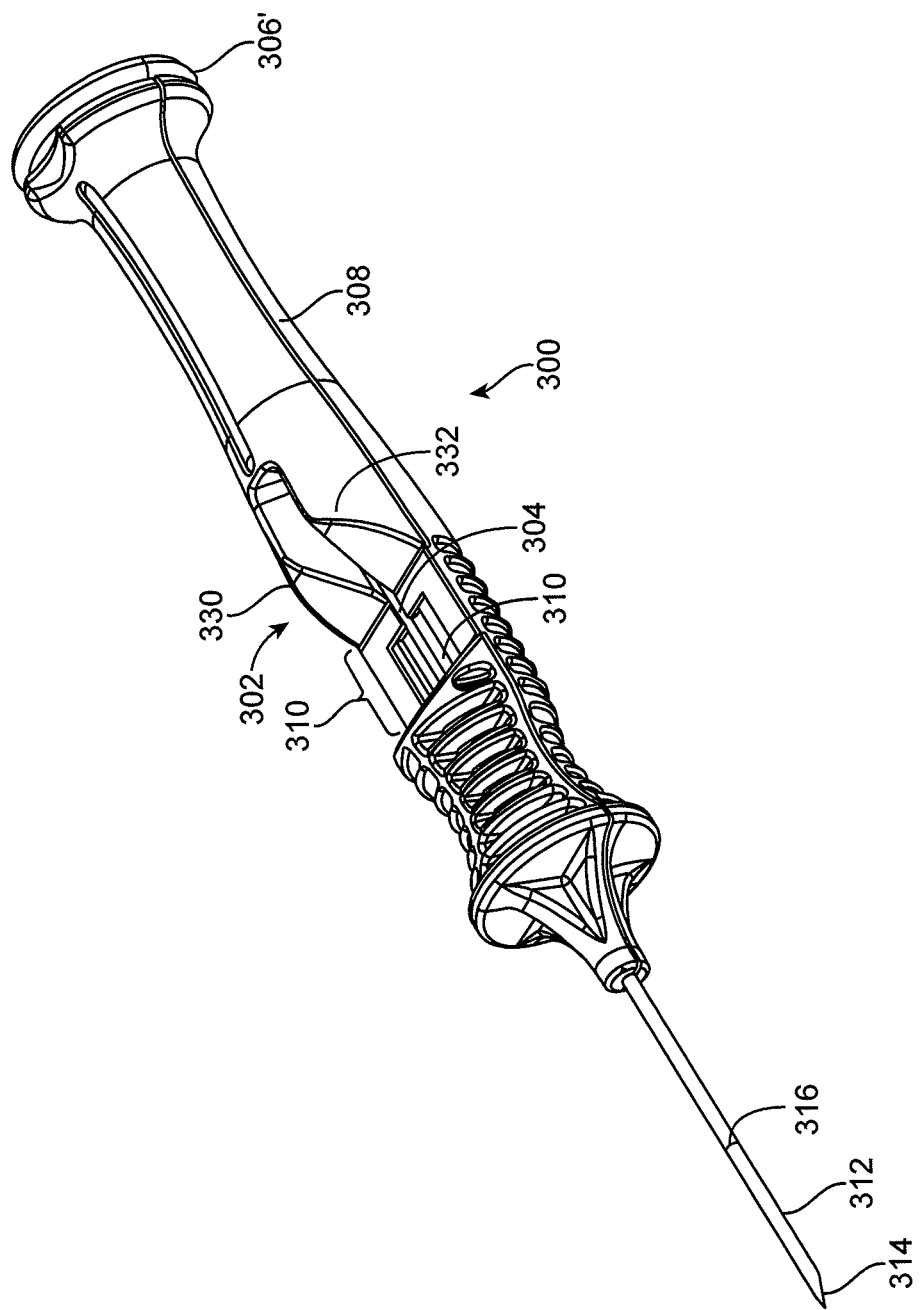
FIGS. 4C-4D show an implant delivery device for after an implant has been placed into a body tissue.

FIG. 4C shows exterior of needle 312 includes marking 316. Marking 316 may indicate a depth to which the needle gets inserted prior to implant deployment. For example, marking 316 may show the location of the proximal end of an implant. Inserting the needle into the tissue up to the marking may ensure that the needle gets inserted to the desired depth (e.g., gets inserted far enough) into body tissue. Actuator 306 includes grippable handle 307 and actuator body 304. Actuator 306 and handle 302 may be adapted to move an implant through (inside) needle lumen and out of an opening at the distal end of the needle when actuator 306 is moved distally. A single delivery tool and actuator may be configured to place multiple implants. Actuator body 309 may move (push) an implant through the delivery tool. Distal end 311 of actuator 306 may be configured to mate with a proximal end of an implant. Distal end 311 may have a smaller, same-size, or larger cross-sectional diameter as a proximal end of an implant. Handle 302 has guide 326. Guide 326 is configured to accept actuator 306. For example, actuator 306 may be moved (pushed) along guide 326 in order to guide the actuator so that the actuator may position an implant, orient an implant, deploy an implant, retract an actuator, etc. A guide may provide guidance to an implant, but in general provides guidance to an actuator. A guide and an actuator may have complementary shapes. For example, a guide may be a trough and an actuator may be a rod that fits partway inside the trough. In general, part of an actuator will sit above a guide when in place in a guide such that the actuator is able to act upon (move) an implant through the delivery tool.

Figure 4D:
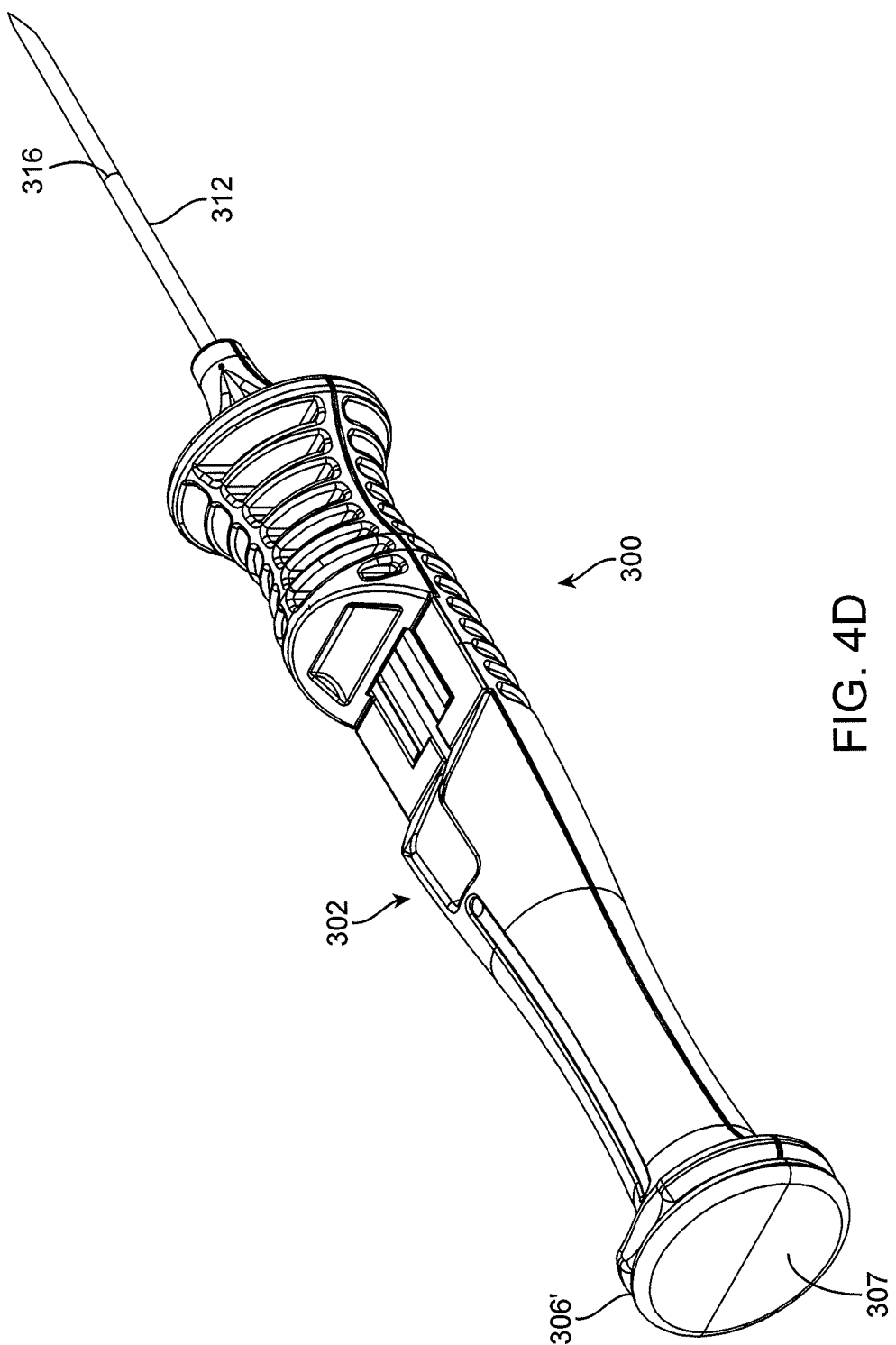
Figure 5A:
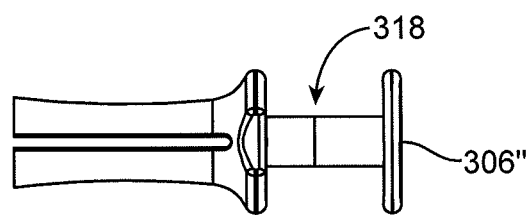
FIGS. 5A-5B show an actuator for an implant delivery device during implant deployment into a body tissue.
Figure 5B:
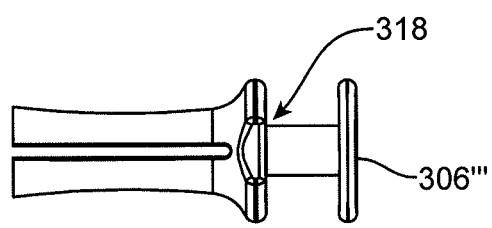

Actuator 306 includes marking 318. Marking 318 may indicate the position of the actuator relative to the delivery tool or implant. For example, marking 318 may be configured to indicate an implant is in the desired location for implant deployment in a tissue, a distal end of an implant is at a distal end of a delivery tool, an implant is in a partially deployed position, an implant is fully delivered (deployed) into a tissue, etc. A marking may be useful to indicate that an implant is in a position, is ready to be deployed (in a pre-deployment position), is partially deployed, or fully deployed. For example, a marker may indicate when the arms of an implant (the fork region) has been deployed and expanded, and the remainder of the implant is in the delivery tool. A marking may be any type of marking, e.g., a line, multiple lines, a thick line, a protrusion, a ring, a color, a fluorescent marker, etc. as long as it provides an indication of the location of the actuator or implant (e.g., relative to the delivery tool). The delivery tool is may be withdrawn from the tissue to finish deploying the implant (e.g., to move the non-arm containing portion of the implant (e.g., implant body) out of the tissue, such as by withdrawing the needle while holding the implant in place (in the tissue) with the actuator. An actuator may include 1, 2, 3, 4, 5, or more than 5 markings for any reason, such as those just described. Additionally, an actuator may have different markings corresponding to different length implants. Actuator 306 may further include a stop mechanism to stop the actuator from traveling further in the delivery tool. FIGS. 4A and 4B show actuator 306 in a deployment position, such as ready to deploy an implant. FIGS. 4C and 4D show actuator 306' in a deployment position, such as during or after implant deployment. FIG. 5A shows actuator 306" before deployment with marking 318 visible. In FIG. 5B marking 318 (which is no longer visible) is aligned with delivery tool to indicate the position the actuator 306'" and that the implant is in place at the tip of the needle in the pre-deployment position. (After deployment, actuator 306 may be in a position such as shown in FIGS. 4C and 4D). Delivery tool 300 may include various features to allow or enable precise placement of an implant, such as markings on the needle, markings on the actuator (plunger), etc.

As mentioned above, an implant may be placed in a minimally invasive way utilizing a small opening in the body to minimize pain and scarring. It may be advantageous however for an implant to be larger than the small opening if, for example, the region of tissue to be treated is larger than the small opening in the body. In such a case, an implant may be placed through the opening in a contracted configuration and may be expanded during or after placement in the body. Additionally, an implant that is expanded during insertion may exert a force on tissues (e.g., which may help hold the implant in place). In some variations, a delivery tool may be configured to accept an implant that is in an expanded configured, contract the implant so that it would fit through the small opening in the body, and then deliver the implant to a body tissue. The implant may be delivered while the implant is in the contracted configuration. An implant may be delivered in an expanded configuration or may be expanded during delivery. A delivery tool may include a loading chamber for loading an implant in an expanded configuration into a delivery tool and one or more shaping chambers to change the shape of the implant. A delivery tool may include an implant loading chamber communicating with the needle lumen and adapted to load a nasal implant into the needle lumen.

Figure 6A:
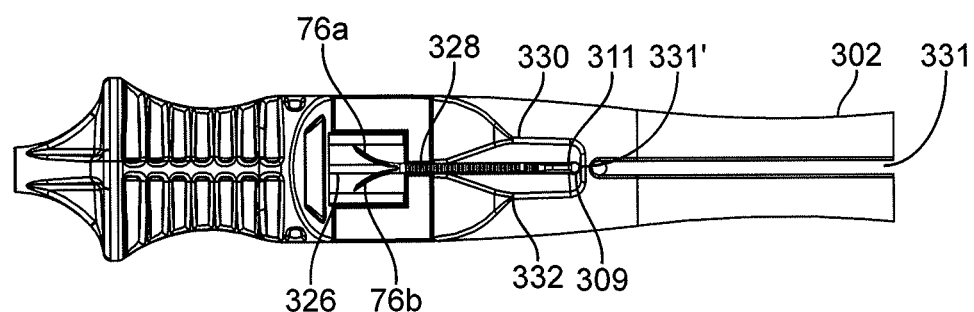
FIG. 6A shows an implant in a loading chamber of an implant delivery device.
Figure 6B:
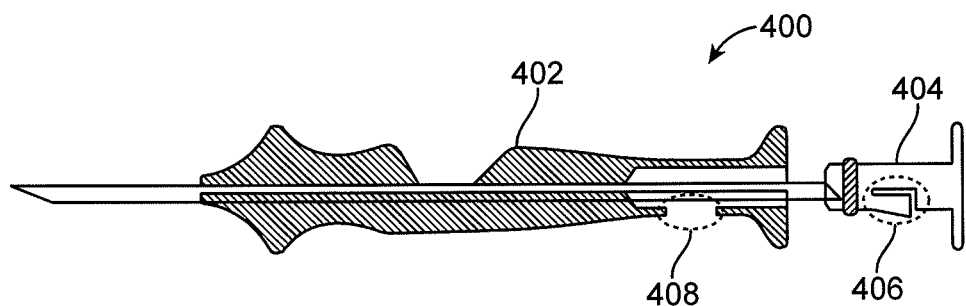
FIG. 6B shows an implant delivery device with a snap feature for audible indication of implant deployment.
Figure 7:
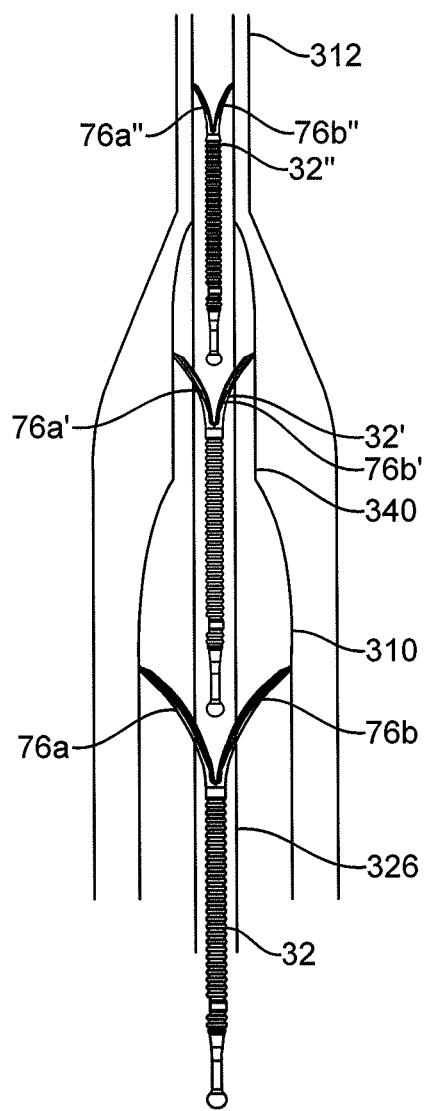
FIG. 7 shows an implant in an implant delivery device changing from an expanded configuration to a contracted configuration in preparation for delivery to a body tissue.

FIG. 6A shows handle 302 with loading chamber 310 for loading an implant into a delivery tool. Loading chamber 310 has an opening (on top) and is configured to accept an implant in an expanded configuration, e.g., with the distal ends of the implant arms spaced apart from each other. FIG. 6A shows handle 302 with implant 32 in loading chamber 310. Implant 32 is in an expanded configuration, with the arms extended away from the central longitudinal axis of the implant. (An implant expanded configuration may be the same as a deployment configuration but may instead be different from a deployment configuration). A loading chamber may generally have a rectangular shape, but could instead have an ovoid or another shape as long as it is able to accept an implant (e.g., in an expanded configuration) and to allow an implant to be moved through the loading chamber (e.g., by a plunger/actuator). A loading chamber may be enclosed on the top (have a roof), but generally will be open on the top to allow insertion of the implant. A loading chamber has a floor and generally has first and second lateral walls (sides) and proximal and distal walls (ends), with the proximal and distal walls each connected (e.g., at either end) with the first and second lateral walls. The proximal and distal walls may each have an opening with the proximal wall opening configured to allow a plunger/actuator to enter the loading chamber and a distal wall opening in open communication with the needle lumen. A proximal wall of loading chamber may have an opening configured to allow the implant or plunger of an actuator to pass through. An implant may be placed (dropped) into the loading chamber from the top so that is lies on the floor of the chamber. FIG. 7 also shows groove 326 for accepting (part of) an actuator/plunger such that the plunger can be moved along the floor of the loading chamber guided by the groove as described above. The plunger may move the implant through and out of the distal end of the loading chamber. The first and second arms 76a, 76b of the implant 32 can be collapsed as the implant enters the proximal end of the needle.

While an entire implant may be loaded directly into a loading chamber, it may be easier to load an implant into a delivery tool using an implant guide. FIG. 6A shows handle 302 with a guide having first side guide 330 and second side guide 332 on either lateral side of a delivery tool handle. The guides, as shown, slope downward to guide an implant (e.g., a proximal end of an implant) of the delivery tool handle floor. Implant 32 may be placed (dropped) in the delivery tool by placing (dropping) the proximal part of the implant onto or between first side guide 330 and second side guide 332, and placing (dropping) the distal part of implant 32 in loading chamber 302. The guides may be generally vertical but may be angled inward towards the floor to help guide the implant into place at the bottom. As shown in FIG. 6A, distal end 331' of plunger 331 is ready to engage the proximal end of implant 32. Implant 32 is moved distally, such as by distal movement of plunger 331, with distal end 331' of plunger 331 engaging the proximal end of implant 32 and moving (pushing) the implant. Plunger 331 may be controlled by a user using handle 307 of actuator 306 and may move implant 32 through and out of the distal end of the loading chamber. Implant 32 may be moved into the lumen of the needle (during which it may change into the contracted configuration), but generally will be moved into a shaping chamber configured to contract the implant into a second configuration. FIG. 7 shows an implant being shaped as it moves along inside a delivery tool. Implant 32 is placed into ovoid loading chamber 311. Implant 32 is moved along loading chamber 311 (e.g., by a plunger/actuator at a proximal end) into shaping chamber 340. In this example, the loading chamber is generally ovoid, and as the implant moves along a distal ovoid end of the loading chamber, resiliently deformable arms 76a, and 76b are shaped (compressed) by the loading chamber, and move inwards towards a central longitudinal axis of the implant. Arms of an implant may be shaped (compressed) as the plunger/actuator moves the implant distally though the delivery tool. Implant 32' and arms 76a' and 76b' are now in the shaping chamber in a partially contracted configuration. In this example, the distal end of the shaping chamber is generally ovoid, and as the implant moves along a distal ovoid end of the shaping chamber, resiliently deformable arms 76a', 76b' are shaped (compressed) by the shaping chamber, and move inwards towards a central longitudinal axis of the implant. The implant is moved into needle 312. Implant 32" and arms 76a" and 76b" are now in the needle in a delivery configuration which may be a fully or mostly contracted configuration. The arms in the contracted configuration may have the same size footprint as the implant. The arms may be in a contracted configuration such that a cross-sectional area through the region of the arms is generally the same size as a cross-sectional area through the implant. The arms may define a cross-sectional area even the arms do not entirely fill the region through the cross-sectional area. The implant may be small enough to move through a needle (e.g., a 14, 16, 18 or other gauge needle). An implant may have a maximum diameter of 2.0 mm, 1.5 mm, 1.2 mm, 1.0 mm, 0.8 mm, or 0.6 mm. Implant 32 may be aided in taking on a contracted configuration by an interaction of a bevel (e.g., a bevel on a radially outward surface of a distal arm end) with an inner wall of the loading chamber or shaping chamber or a needle lumen. Although shown with an implant with two arms with bevels, an implant may have no bevels, a single bevel, a bevel on each arm, two bevels on each arm, etc. and may have 0, 1, 2, 3, 4 or more arms.

Shaping the implant as described using a loading chamber, shaping chamber and needle may instead be performed in other ways as long as the implant is moved from an expanded configuration to a contracted configuration in the delivery tool. For example, an implant delivery tool may have only a loading chamber and the loading chamber may shape an implant as described above without use of shaping chamber; the implant may travel directly from the loading chamber to the needle. An implant delivery tool may have multiple shaping chambers and each may partially change the implant configuration. A shaping chamber may be ovoid or may be rectangular, etc.

In some variations an implant may be implanted into a tissue of a body using a delivery device following one or more of the following steps: palpating the implant delivery site and determining an implant location; retracting the plunger from the delivery handle until it is clear of the loading chamber. As shown in FIG. 6A, place the implant flat in the loading chamber; positioning the implant in the tip of the needle by slowly advancing the plunger until the marker on the plunger is flush with the back of the delivery device handle; verifying that the tips of the implant arms (fork) are visible at the base of the implant tip bevel and are in the same plane as loaded; inserting the needle into the mucosal side of the nasal tissue; advancing the cannula (e.g., until the tip is sufficiently (e.g., approximately 4 mm) away from the target end location and palpating the needle location); verifying that the marker on the needle approximates the mucosal surface at the insertion point; verifying the delivery tool orientation so that the arms (forks) are in the correct plane; advancing the plunger on the delivery device to a fully depressed position; deploying the implant; (e.g., to thereby deploy the implant beyond the distal tip of the needle to engage with the tissue); slowly withdrawing the needle from the tissue.

Figure 8:
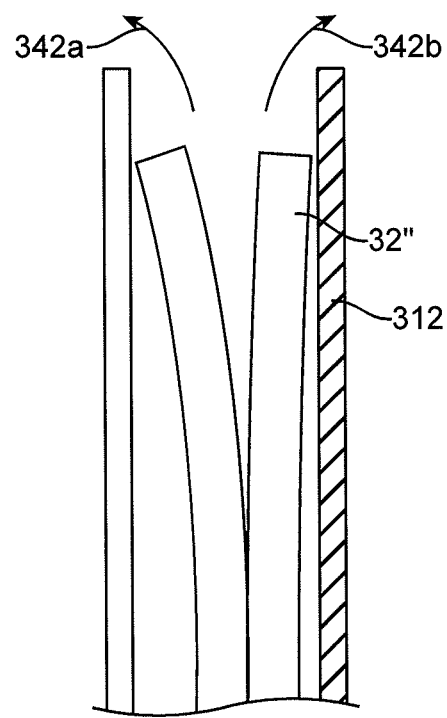
FIG. 8 shows deployment of an implant from a needle of an implant delivery device into a body tissue.

An implant may take on a different shape or different configuration as it is implanted (during implantation as it moves out of the needle and into the body tissue). Implant 32 may move from a delivery configuration towards a deployment configuration during implantation in a tissue. An implant may move from a contracted or compressed configuration to an expanded configuration by one or more distal arms moving away from a central longitudinal axis of the implant. The arms (e.g., distal ends) of the arms may be biased to move away from a central longitudinal axis. FIG. 8 shows implant 32" inside needle 312 during deployment. Arrows 342a and 342b show the movement arms 76a" and 76b" will take as they move out of the needle and into tissue. The arms may move go straight out, but in general will diverge away from a central longitudinal axis such that the distal ends of the arms are bent. Tissue may be trapped between the arms. Diverging arms may help distribute forces across a wider area of tissue. In nasal tissue, tenting and distal migration may be prevented or minimized. Diverging arms may also keep the implant in place as the needle or delivery device are removed. Bevels may help the arms diverge. Arm movement may be aided in moving through tissue by a bevel on a radially inward surface of the distal end of the arm. The bevel may cut through tissue and guide the arm through the tissue. Although shown with an implant with two arms with bevels, an implant may have no bevels, a single bevel, a bevel on each arm, two bevels on each arm, etc. and may have 0, 1, 2, 3, 4 or more arms. The implant may be advanced (pushed) into body tissue by an actuator/plunger.

An implant in a contracted position may be deployed directly into tissue to move from a contracted configuration to a delivery configuration, but generally may be oriented before deployment. An implant may be oriented in the delivery tool handle, but generally is oriented in the needle. An implant may be oriented by a non-circular lumen (in either the delivery tool handle or in the needle). A non-circular lumen with a major axis and a minor axis may allow the arms of the implant to diverge (slightly) in the outward direction of the major axis (and away from the central longitudinal axis), thus orienting the implant (via the arms) in the direction of the major axis. This may occur, for example, as the plunger is moving the implant through the implant tool handle but generally will happen as the implant is moving through the needle. In some examples, after the implant is oriented, the needle may have a circular cross-sectional region and the implant may travel through the circular cross-sectional region, but maintain its orientation. For example, the distance travelled through the circular cross-sectional region may be relatively short.

An implant may move from a delivery configuration within the needle lumen toward a deployment configuration outside the needle lumen. As the implant exits the distal end of the needle, the arms may travel away from each other (diverge). The implant may be fully deployed before the implant tool is removed away from the implant or the implant may be partially deployed (e.g., the arms may be deployed but the rest of the implant may be disposed inside the needle of the delivery tool, and, once the arms are deployed, the needle may be removed away from the implant and away from the tissue to leave the implant in place). In some examples, the actuator may push the implant further into tissue (aided by inner bevels on the arms to move the arms through the tissue). In other examples, the actuator may hold the implant in place as the delivery tool is removed away from the implant and the actuator, and then the actuator is removed, leaving the implant in place in the tissue. The implant may move through tissue aided by the inner bevels that cut through tissue and/or by the biased arms attempting to return to their unbiased configuration. An implant may move from a deployment configuration towards a delivery configuration as it exits the distal end of a delivery device.

In some embodiments advancing the implant includes pushing the implant distally such that the first arm and second arm of the implant each engage the tissue thereby moving away from the central longitudinal axis of the implant. In some embodiments advancing the implant can include retracting a portion of the delivery tool, such as the needle, to allow the first arm and second arm of the implant to self-expand such that the arms move away from the central longitudinal axis of the implant. In some cases advancing can include a combination of pushing and retracting. For example, advancing the implant can include pushing the implant distally and retracting a portion of the delivery tool such that the first arm and second arm each engage the tissue thereby moving away from the central longitudinal axis of the implant.

The first arm and second arm of the implant can each form an incision path as the implant engaged with the tissue. For example, advancing the implant can include the first arm forming a first arm incision path with the first arm incision path having a longitudinal axis that is offset from a longitudinal axis of the delivery tool. Advancing can also include the second arm forming a second arm incision path with the second arm incision path having a longitudinal axis that is also offset from a longitudinal axis of the delivery tool. The longitudinal axis formed by the first arm incision path and the second arm incision path can include a curved or arced shape. The first arm incision path and second arm incision path can form an angle that is less than 180 degrees. Advancing the implant can also include the first arm and second arm each engaging a portion of tissue located between the first arm and the second arm.

Figure 9A:
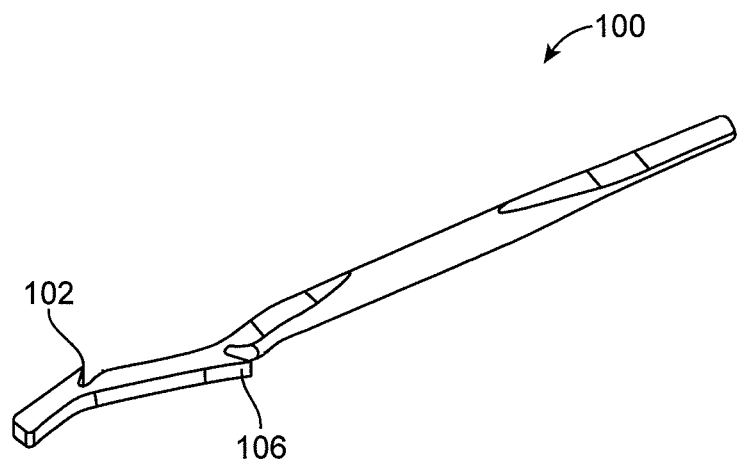
FIGS. 9A-9B show an implant in deployed and delivery configurations for placement in a body tissue.
Figure 9B:
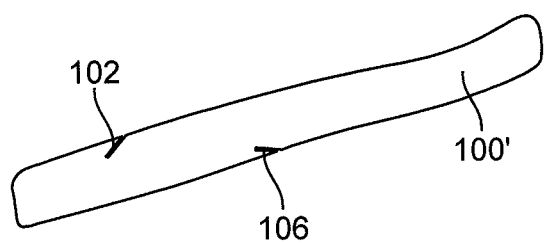
Figure 11A:
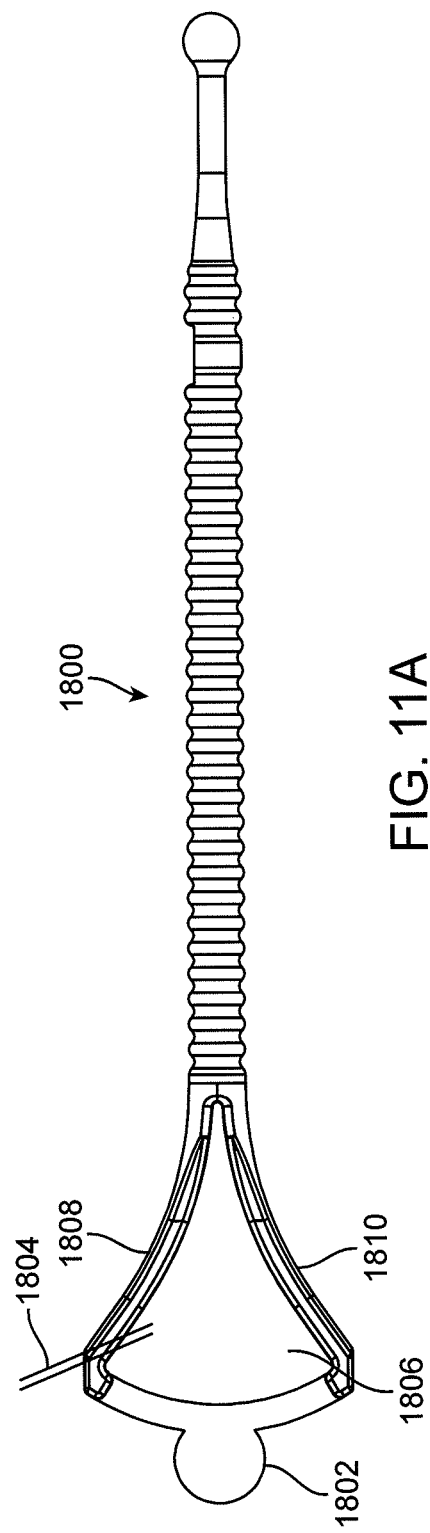
FIGS. 11A-11B show drawings of a molded implant with beveled ends.
Figure 11B:
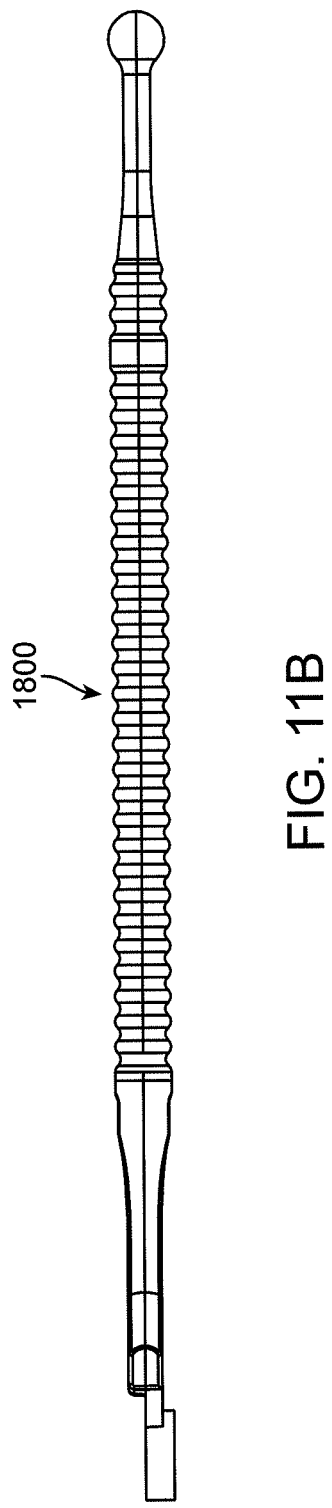

FIG. 9A shows implant 100 in a deployment configuration. The same implant is shown in FIG. 9B in a delivery configuration. Implant 100 has first hook 102 and second hook 106. A hook may be useful for catching or holding body tissue and holding or anchoring the implant in place in a tissue. A hook may be curved or bent so as to form an angle, e.g., of up to 30°, from 30° and up to 45°, from 45° and up to 60°, from 60° up to 90° or 90° with the implant at the base of the hook or with a centerline of the implant. An implant may be curved or bent relative to or towards the proximal end as shown in FIG. 9A, or may be curved or bent relative to or towards the distal end. A hook angle may be chosen for any reason. For example, a smaller angle may be chosen to minimize the overall size ("footprint") of an implant; such an implant may fit into a smaller space. A larger angle may be chosen, for example, to spread resistive force (holding the implant) over a greater surface area or over different tissue types; such an implant may cause formation of a larger area of scar tissue to better support the nasal valve and reduce nasal valve collapse. An implant may have one or may have more than one hook. An implant with more than one hook may have the hooks opposite each other (e.g., relative to the implant midline) or two or more hooks may be offset from each other, such as shown in FIGS. 9A-9B. An implant with a hook (a hooked implant) may be placed in body tissue in a contracted form and, once inside the tissue, may expand and thereby catch or hook body tissue to hold the implant in place in the tissue. A hook on an implant may expand in a body tissue due to the removal of a force (e.g., removal from an inserter that has been holding or compressing the implant), an addition of a force (e.g., by manipulation of the implant in the tissue with a tool, or in response to a stimulus. As shown in FIGS. 9A-9B an implant with a hook may have an expanded configuration and a contracted configuration. In an expanded configuration, a hook may extend (e.g., at an angle) from a body or side of an implant. In a contracted configuration, a hook may lie close to a main implant axis or may fit into or be partially or fully recessed into the main implant body. FIG. 9B shows an implant in which the implant bends or folds inward towards a central longitudinal axis to form a contracted or delivery configuration. In this example, first and second hooks 102' and 106' may lie close to or flush against the body of the implant when in a contracted or delivery configuration. A hook may be biased towards expansion and may be held contracted in place close to or in contact with the implant body by a force from a lumen of a delivery tool or needle (such as described above). A pair of (biased) hooks on an implant may offset each other to create an implant with a substantially longitudinal axis (when contracted or expanded). For example, such an implant may have local areas wherein the main implant axis bends or turns. An implant with a single hook may have a longitudinal axis, but may instead have an axis that curves towards (or away from) the hook. A hook on an expanded hooked implant may be contracted as it moves into or through a delivery tool to thereby fit into a needle; the hook portion may be compressed by the needle.

Implant 100 may have an expanded configuration and a contracted configuration. In some variations, an implant with a hook may have a contracted configuration when inside a delivery tool or needle. In some embodiments, a hook may be in a contracted configuration and an implant placed inside a delivery device with a hook in the contracted configuration and may be held by the delivery device in a contracted form. In other variations, an implant may be in an expanded form and may be guided or shaped by a delivery device into a contracted configuration.

An implant may be made of any biocompatible material that provides the desired support and shaping properties of the implant. An implant may be partially or wholly made from a non-biodegradable material as known in the art such as any polymer, metal, or shape memory material. An implant may be made from organic and/or inorganic materials. A material of the implant may be solid, (e.g. titanium, nitinol, or Gore-tex), braided or woven from a single material (such as titanium, or Polyethylene Terephthalate, or a combination of materials). A woven material may have pores which allow ingrowth of tissue after implantation. Representative synthetic polymers include alkyl cellulose, cellulose esters, cellulose ethers, hydroxyalkyl celluloses, nitrocelluloses, polyalkylene glycols, polyalkylene oxides, polyalkylene terephthalates, polyalkylenes, polyamides, polyanhydrides, polycarbonates, polyesters, polyglycolides, polymers of acrylic and methacrylic esters, polyacrylamides, polyorthoesters, polyphe azenes, polysiloxanes, polyurethanes, polyvinyl alcohols, polyvinyl esters, polyvinyl ethers, polyvinyl halides, polyvinylpyrrolidone, poly(ether ketone)s, silicone-based polymers and blends and copolymers of the above.

Specific examples of these broad classes of polymers include poly(methyl methacrylate), poly(ethyl methacrylate), poly(butyl methacrylate), poly(isobutyl methacrylate), poly(hexyl methacrylate), poly(isodecyl methacrylate), poly (lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), poly(vinyl acetate), poly(vinyl chloride), polystyrene, polyurethane, poly(lactic acid), poly(butyric acid), poly(valeric acid), poly[lactide-co-glycolide], poly(fumaric acid), poly(maleic acid), copolymers of poly (caprolactone) or poly (lactic acid) with polyethylene glycol and blends thereof.

A polymer used in implants may be non-biodegradable. Examples of non-biodegradable polymers that may be used include ethylene vinyl acetate (EVA), poly(meth)acrylic acid, polyamides, silicone-based polymers and copolymers and mixtures thereof.

In some embodiments the implant can include one or more bioabsorbable materials in combination with a non-absorbing material. For example, in some cases at least one of the distal end, proximal end, or central portion is composed of a core made of a non-absorbable or an absorbable material. The implant can then include an outer layer made of a different non-absorbable or absorbable material from the core. In some examples the core and outer layer are fixedly laminated to one another. In other examples the core and outer layer are slid-ably engaged with one another.

In some embodiments the first and second arms of the implant are configured to self-expand toward the deployed configuration. In some embodiments the first and second arms of the implant are configured to move to the deployed configuration through engagement with tissue or part of the delivery tool.

For example, an implant or arms or features on an implant may include shape memory material. In some variations, an implant includes a biocompatible, bioabsorbable material such as a bioabsorbable polymer. A bioabsorbable or biodegradable implant may provide structure and support to a body tissue, such as nasal tissue, for a temporary period of time and may induce or cause the formation of scar or other tissue that provides structure and support to the body tissue for a longer period of time, including after the implant is degraded. Biologically formed scar or other tissue may be beneficial because it may be more comfortable, provide longer term support, stay in place better, etc. than does an implant. Part or all of an implant may be degradable in vivo (also referred to as biodegradable) into small parts and may be bioabsorbable. An implant or implant body may consist essentially of a bioabsorbable material. An implant or implant body may include two or more than two different bioabsorbable materials. A method as described herein may include biodegrading and bioabsorbing an implant or just part of an implant if an implant includes both bioabsorbable and non-bioabsorbable parts. Bioabsorbing may be facilitated by tissues and organs. Tissues and organs that bioabsorb may include bodily fluids, such as blood, lymph, mucus, saliva, etc. Bacteria may also aid in bioabsorbing a material. An implant may be partially or wholly made from one or more biocompatible biodegradable material, such as from a naturally occurring or synthetic polymer. A biodegradable implant may be made from a poly(lactide); a poly(glycolide); a poly(lactide-co-glycolide); a poly(lactic acid); a poly(glycolic acid); a poly(lactic acid-co-glycolic acid); poly(lactide)/poly(ethylene glycol) copolymers; a poly(glycolide)/poly(ethylene glycol) copolymers; a poly (lactide-co-glycolide)/poly(ethylene glycol) copolymers; a poly(lactic acid)/poly(ethylene glycol) copolymers; a poly (glycolic acid)/poly(ethylene glycol) copolymers; a poly (lactic acid-co-glycolic acid)/poly(ethylene glycol) copolymers; a poly(caprolactone); poly(caprolactone)/poly (ethylene glycol) copolymers a poly(orthoester); a poly (phosphazene); a poly(hydroxybutyrate) or a copolymer including a poly(hydroxybutyrate); a poly(lactide-co-caprolactone); a polycarbonate; a polyesteramide; a polyanhydride; a poly(dioxanone); a poly(alkylene alkylate); a copolymer of polyethylene glycol and a polyorthoester; a biodegradable polyurethane; a poly(amino acid); a polyetherester; a polyacetal; a polycyanoacrylate; a poly (oxyethylene)/poly(oxypropylene) copolymer, or a blend or copolymer thereof. In some examples, an implant includes poly-L-lactic acid (PLLA) or poly-D-lactic acid (PDLA) or both. In some examples, an implant is 90:10, 80:20, 70:30, 60:40, 50:50 PLLA/PDLA copolymer or is in between any of these values. In some examples, an implant is 70:30, +/−10% PLLA/PDLA copolymer.

The implant can have different sections made out of different bioabsorbable materials based on the desired characteristics for each section and based on the type of tissue that each section engages with and the typical properties of the type of tissue. It can be desirable for the arms and central section of the implant to provide structural support longer than the proximal end. For example the arms and central portion can be made of a first bioabsorbable material having a first bioabsorption profile and the proximal end can be made of a second bioabsorbable material having a second bioabsorption profile. The second bioabsorption profile can be shorter than the first bioabsorption profile.

A biodegradable implant or portion of an implant as described herein may be configured to biodegrade (to be absorbed) in less than 60 months, 36 months, less than 24 months, less than 18 months, less than 12 months, less than 9 months, less than 6 months, less than 3 months, or less than 1 month, or any time in between any of these times. For example, an implant may be configured to degrade from between 9 months and 12 months, between 3 months and 12 months, between 1 month and 12 months, etc. If an implant is entirely made up of biodegradable material, then the entire implant may degrade or mostly degrade in these times. For example, a biodegradable implant may degrade so that is has significantly altered material properties. The material properties of a bioabsorbable implant change over time; thus a bioabsorbable implant be configured to have any of the material properties, such as those described elsewhere herein after any of the above periods of time in a body or exposure to a body fluid. In some examples, a bioabsorbable implant has (or is configured to have) a flexural rigidity of less than 15 N-mm2, less than 10 N-mm2, less than 5 N-mm2, less than 4.2 N-mm2, less than 4 N-mm2, less than 3 N-mm2, less than 2 N-mm2, or less than 1 N-mm2 after 3, 6, 9, or 12 months in a body. If an implant includes both biodegradable and non-biodegradable material, then the biodegradable portion may degrade in any of these time periods and the non-biodegradable material may not degrade. An implanted implant in a body may be exposed to body tissues and body fluids to cause biodegradation. An implant may be chosen or configured to biodegrade within the listed times for various reasons. For example, an implant with the desired material properties (e.g., flexibility, strength, etc.) that is exposed to mucous may degrade within a different time frame than an implant that is not exposed to mucus. An implant that degrades more slowly may allow more time for desired scar or other tissue to form before it degrades.

An implant may include additional materials, such as an antibiotic, another antibacterial agent, an antifungal agent, an antihistamine, an anti-inflammatory agent, a cartilage growth inducer, a decongestant, a drug, a growth factor, microparticles, a mucolytic, a radiopaque material, a steroid, a vitamin, etc. Such materials may be attached to, adhered to, coated onto, or incorporated into to an implant. Such materials may be inserted into a body tissue along with the implant. Such materials may be required at different times and may be time sensitive or time release. For example, an anti-inflammatory agent may be useful immediately after implantation to prevent too much early inflammation and pain, but may not be desirable during later stages of scar formation and healing as it may interfere with a healing process that provides new tissue to provide support for tissues once the implant is remove. For example, an implant may be configured to release a cartilage growth inducer, such as a fibroblast growth factor (FGF; such as basic fibroblast growth factor or FGF2) or a transforming growth factor (TGF; such as TGFβ1) after several days or weeks so as to prevent an inappropriate or unwanted response early on.

EXAMPLES

Implant testing in nasal tissue. FIGS. 10A-10B show multiple implants 32 implanted in the nose of the patient to support the area of maximum collapse at the posterior point of the junction of the upper and lower lateral cartilages.

Flexural rigidity determination. Flexural rigidity was determined for absorbable nasal implants and for implantable sheets.

Flexural Rigidity is also known as bending stiffness and this property represents the resistance of an object to deflection from bending forces. Flexural Rigidity is defined as the product of the Flexural Modulus (E) and the Second Moment of Inertia (I) of the test article about the bending axis of interest. Flexural Rigidity=E*I.

To understand the relevance of Flexural Rigidity examine the two parameters which are multiplied to obtain Flexural Rigidity. First is the Flexural Modulus (also termed Bending Modulus) which is a ratio of the amount of stress imparted to a component to the amount of bend which results from that stress. Stress is defined as force per unit area, so it is important to note that Flexural modulus is a value which is determined by the material properties alone and is not dependent on the shape of a given component. This means that for a specific material, a fixed force per unit area will result in the same amount of strain (deformation) regardless of the shape of the component. This value is typically empirically derived for various materials via a three point bend test of a test article having a well-established cross sectional area. Alternatively tensile modulus (also known as Young's Modulus) can be substituted because it is nearly identical for most homogeneous and isotropic materials and is easier to obtain via a tensile test. Flexural Modulus is summarized as being the measure of the inherent relationship between bending stress and the resulting deformation, independent of the material's shape.

The second parameter multiplied to obtain Flexural Rigidity is the Second Moment of Inertia (I). This is a geometric property of a specific component which reflects how the points which make up the cross section are distributed with respect to a chosen axis. For the purposes of calculating Flexural Rigidity the Second Moment of Inertia represents the contribution of the size and shape of a component to its resistance to deflection from bending forces.

The descriptions above demonstrate that a component's resistance to deflection from bending forces (Flexural Rigidity) is determined by both the stress/strain response of the raw material, and by the specific shape and the orientation of that shape when subjected to bending forces.

Flexural Rigidity or Bending Stiffness is a useful property to specify the resistance of a structure to bending forces. The Flexural Rigidity incorporates both the contribution of the material's stress-strain response as well as the specific geometry of the structure. Flexural Rigidity was tested on absorbable implants, both sheet and rod configurations. An implant with a Flexural Rigidity substantially equivalent to healthy cartilage may be well suited to supporting weakened cartilage, cartilage which is healing, or soft tissue which lacks adequate support from adjacent cartilage.

In order to compare the Flexural Rigidity of the implantable devices to the Flexural Rigidity of healthy cartilage information about the size, shape, and cartilage modulus of elasticity for the type of cartilage that is commonly used in nasal surgery to support weakened or healing cartilage and adjacent soft tissues is first obtained. Literature references the use of septal cartilage as the preferred source of cartilage graft material due to its strength and its straightness. (Pochat V D, MD, Meneses J V L, MD, PhD, "The Role of Septal Cartilage in Rhinoplasty: Cadaveric Analysis and Assessment of Graft Selection," Aesthetic Surgery Journal, 31(8) 891-896 (2011). The size and shape of a cartilage graft depend on the application, the source of the graft material, the anatomy of the patient and the physician preference. An alar batten graft is an appropriate graft to use for comparison with the implantable devices because it is a graft often used to add structure to the nasal lateral wall (lower and upper lateral cartilages, and adjacent soft tissue) and is intended to improve nasal airflow by preventing the nasal valve from collapsing down during inspiration. (Millman, MD, "Alar Batten Grafting for Management of the Collapsed Nasal Valve," The Laryngoscope 112, (March 2002)). This is an important clinical need; the devices described herein may be well suited for. The standard of care for alar batten grafts is the use of septal cartilage trimmed into an oval or a rectangular shape which varies according to the patient anatomy. An approximate range for graft width is 6-12 mm. The average thickness of a section of extracted septal cartilage ranges from 1 to 1.7 mm. (Pochat, op cit). Literature also provides a range of modulus of elasticity for septal cartilage ranging from 5 to 32 MPa. (Westreich R W, William Lawson, MD, D D S, et al, "Defining Nasal Cartilage Elasticity: Biomechanical Testing of the Tripod Theory Based on a Cantilevered Model," Arch Facial Plast Surg, 9(4)264-270 (2007). Assuming a graft of rectangular cross section, the Flexural Rigidity ranges from 10 to 590 N*mm^2. This range represents the occurrence of all minimum conditions and all maximum conditions. In reality, this is unlikely especially with regards to the thickness and the modulus of elasticity. Westreich et al. have reported that modulus of elasticity is significantly higher when the septal cartilage is not trimmed down to a reduced thickness. It is likely that a thick septum would be trimmed and have a lower modulus whereas a thin septum would not be trimmed and would maintain a higher modulus. A reasonable expected range for septal flexural rigidity of a graft typical of alar batten graft usage is 50 to 130 N*mm^2. This range is obtained with the following assumptions: Minimum flexural rigidity conditions: 5 MPa modulus, 1.7 mm thickness, and 6 mm width. Maximum flexural rigidity conditions: 32 MPa modulus, 1 mm thickness, 12 mm width. Described herein are Flexural rigidity of the INEX absorbable implants within this range of Flexural rigidity in order to provide a supporting structure with a rigidity similar to that of an alar batten graft comprising septal cartilage.

Mechanical Testing. This testing assesses the Flexural Rigidity of multiple shapes of an Implantable Sheet including a single rod subset which is directly applicable to the center structural section of the Gen 2 Absorbable Nasal Implant. In addition test data is also presented for other absorbable and non-absorbable polymer implants which are also indicated for use in nasal surgery.

Objective. To quantify the Flexural Rigidity of the INEX Implantable Sheet in (various shapes), the Ethicon PDS™ Flexible Plate (various shapes), and Medpor® Surgical Lateral Nasal Valve Implant using a 3-point bend test setup.

Test Articles:

A: Ethicon PDS™ Flexible Plate a. Product Dimensions: 0.5×40×50 mm [Tested in various trimmed geometries—See Table A]

b. Catalog Number: N/A c. Lot CL9KMRZ0 Exp. December 2015

B: Medpor® Surgical Implant, Lateral Nasal Valve a. Product Dimensions: 13×3.5×85 mm b. Catalog Number: 7545 c. Lot F268A01 Exp. February 2019

C: INEX Implantable Sheet a. Product Dimensions: 1.1×24.5×20.0 mm [Tested in various trimmed geometries—See Table C]

b. Catalog Number: Spiro IM01 c. Lot 161245 [Spectrum Plastics Group]

Method and General Setup. Each type of sample was setup in a 3-point bend configuration with simple supports as defined in ASTM Standard D790-10: Flexural Properties of Unreinforced and Reinforced Plastics and Electrical Insulating Materials. The figures below show how each sample was loaded and supported. Two pin gauges were adhered to a vise jaw. This setup enables the tester to adjust the jaw separation width as needed.

The setup used represents a modification to the default setup defined in D790-10 which is an acceptable practice per the standard. The standard states that the supports and loading tips used are to have a 5 mm radius [0.197 in]. For this testing the two lower supports used were 0.060 in [1.53 mm] dowel pins. This is appropriate given the small size of the test samples. Three different loading tips were used due to sample geometry; both large and small chisel point tips and a round plunger. The large and small chisel point tips feature flat loading surfaces 1.5 mm [0.059 in] and 1.0 mm [0.039 in] respectively. The round tip plunger has a radius of 4 mm [0.157 in]. Refer to Table A for the application of each loading tip style.

Equipment. Calipers (CAL109) were used to verify the support width for each test setup specified in Table A.

Mark-10 acquisition software [MEAURgauge V1.8.2] was used to read all force and displacement data to an excel file. The data acquisition rate was set to 20 points per sec [20 Hz]. The test stand was set to load the samples at a rate of 1 in/min in the compressive direction. Each individual test article was setup and tested per the specific parameters shown in Table A.

Data Analysis: Data collected is in the form of force vs. displacement curves. From these curves, the initial linear portion is isolated and the slope is computed in Excel by using a linear trendline. Flexural Rigidity is defined as the product of the Flexural Modulus (E) and the Area Moment of Inertia (I). Flexural Rigidity can be calculated by using the Force/Displacement slope obtained from the test data by solving the equation for center deflection of a simply supported beam as shown in FIG. 10C.

$$\delta = \frac{Pl^3}{48EI}$$

is rearranged to solve for Flexural Rigidity $$(E*I)\ EI = \left(\frac{P}{\delta}\right)\left(\frac{l^3}{48}\right)$$

$$\left(\frac{P}{\delta}\right) = \text{Force/Displacement slope}$$

$$\left(\frac{l^3}{48}\right)$$

is a constant based on the width of the test supports

The calculations for Flexural Rigidity are shown on each chart and are calculated based on the average Force/Displacement slope from two test samples.

Results summary:

| Device | Test Article Designation/Description | AVG Flexural Rigidity (N*mm$^2$) |
|---|---|---|
| PDS Flexible Plate | A.1 - 1.25 mm Strips (2 Layers) | 20.9 |
| PDS Flexible Plate | A.2 - 10 mm Plates (2 Layers) | 244.8 |
| PDS Flexible Plate | A.3 - 1.5 mm Strip | 9.0 |
| PDS Flexible Plate | A.4 - 10 mm Plate | 114.5 |
| MedPor Lateral Nasal Valve | B.1 - Strong Side | 141.7 |
| MedPor Lateral Nasal Valve | B.2 - Weak Side | 114.97 |
| INEX Implantable Sheet | C.1 - Single Rod | 78.98 |
| INEX Implantable Sheet | C.2 - Plate Shape (Strong Direction) | 380.9 |
| INEX Implantable Sheet | C.3 - Plate Shape (Weak Direction) | 101.5 |
| INEX Implantable Sheet | C.4 - Oval Batten Graft Shape | 214.3 |
| INEX Implantable Sheet | C.5 - Narrow Batten Graft Shape | 217.1 |

CONCLUSION

The test data shown above indicates that the single rod subset of the INEX Implantable Sheet has a Flexural Rigidity of approximately 80 N*mm$^2$ which is comparable to the expected range of Rigidity for a batten graft formed of septal cartilage (50-130N*mm$^2$). The Gen 2 Absorbable Nasal Implant has a structural section which is equivalent to the aforementioned single rod subset. Therefore the Absorbable Nasal Implant also has a Flexural Rigidity comparable to the expected range of Rigidity for a batten graft comprised of septal cartilage.

FIGS. 11-14 show examples of implant delivery systems, implant delivery tools and implants similar to the implants and delivery systems discussed above. FIGS. 11A-11B show drawings of a molded implant 1800 with beveled ends having a holding element 1802 for use in manufacturing. After forming the device, cuts may be made along lines 1804 and 1806 to create beveled ends of the arms 1808 and 1810, respectively, such as the 63 degree trim angle shown.

FIGS. 12A-12C show drawings of a molded implant with beveled ends. As shown, the overall length of the device 1900 may range from 0.74 inches to 1.04 inches. Arms 1902 and 1904 have an at-rest spread at their tips of 0.166 inches to 0.206 inches. These drawings exemplify dimensions that may be employed for the implants of this invention, as discussed in more detail above. Detail A of FIG. 12C illustrates the intersection of arms 1902 and 1904 at point 1906. The intersection of arms 1902 and 1904 at point 1906 forms an angle. The angle illustrated in FIG. 12C is an acute angle less than 90°. In some embodiments the arms 1902 and 1904 can engage with tissue such that the arms 1902, 1904 form an angle that is less than 90°. In some embodiments the angle between the arms 1902, 1904 is less than 180° when the implant is implanted in the tissue.

Figure 13A:
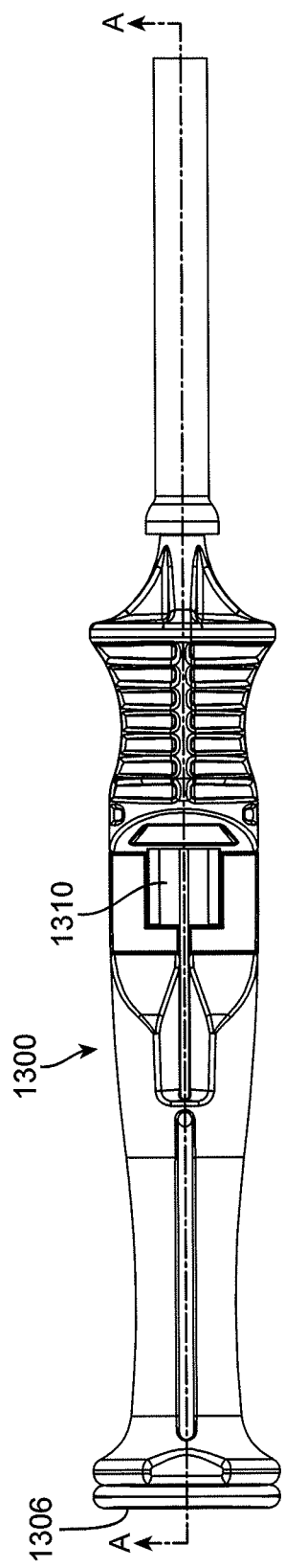
FIGS. 13A-13B show drawings of an implant delivery device.
Figure 13B:
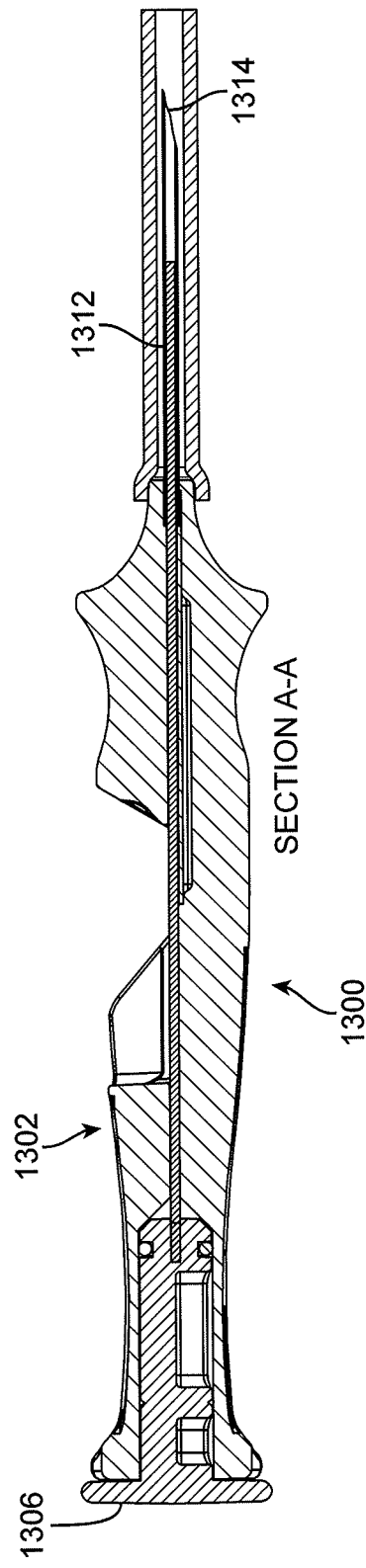
Figure 14:
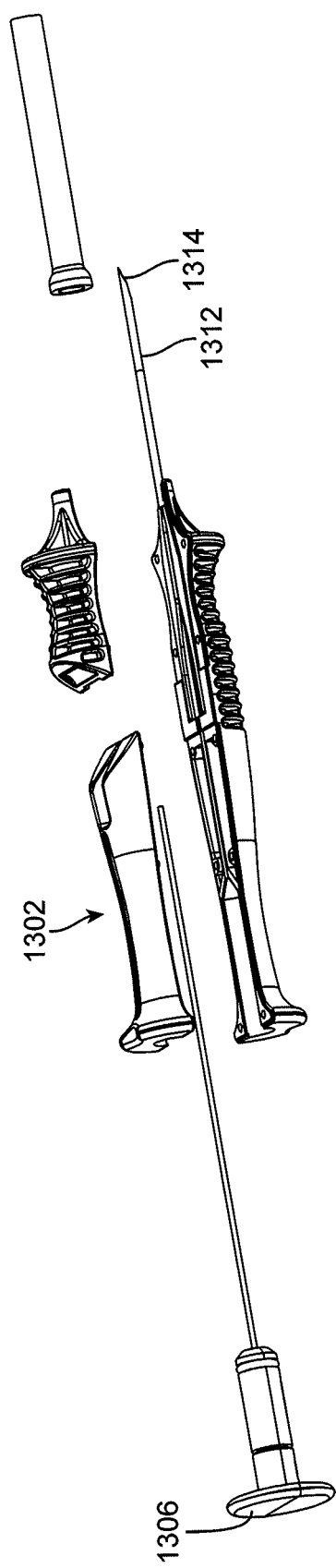
FIG. 14 shows drawings of an implant delivery device.

FIGS. 13A-13B and 14 show drawings of an implant delivery device 1300 having a handle 1302, actuator 1306, implant loading chamber 1310, with needle 1312 having a sharp distal end 1314.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

We claim:

1. A system comprising:
 a nasal implant delivery tool, the nasal implant delivery tool including:

a handle,
a needle extending distally from the handle, the needle having a needle lumen with a non-circular cross-section having a major axis and a minor axis and a sharp distal end, and
an actuator configured to move a nasal implant along the needle lumen and out of an opening at the sharp distal end of the needle; and
a nasal implant disposed in the needle lumen and including first and second arms at a distal end of the nasal implant, the first and second arms each having a proximal end fixed to the nasal implant and a distal end not fixed to the nasal implant, wherein the distal end of each of the first and second arms is biased to move away from a central longitudinal axis of the nasal implant from a delivery configuration within the needle lumen toward a deployed configuration outside of the needle lumen,
wherein the first arm and the second arm of the nasal implant each include a bevel on a radially inward surface of the distal end.

2. The system of claim 1, further comprising an implant loading chamber communicating with the needle lumen and configured to load the nasal implant into the needle lumen.

3. The system of claim 2, wherein the implant loading chamber is configured to move the nasal implant from the deployed configuration to the delivery configuration as the nasal implant is advanced into the needle lumen.

4. The system of claim 1, further comprising an actuator register configured to indicate a position of the actuator at which the nasal implant is at the distal end of the needle lumen.

5. The system of claim 4, the actuator register comprises one or more markings on the actuator or on the handle.

6. The system of claim 1, further comprising an actuator register configured to indicate a position of the actuator at which at least a distal portion of the nasal implant has been moved out of the needle lumen.

7. The system of claim 6, wherein the actuator register is a stop element preventing further movement of the actuator.

8. The system of claim 1, wherein the nasal implant delivery tool further includes an indicator configured to provide a signal that the nasal implant has been moved out the needle lumen.

9. The system of claim 1, wherein the nasal implant includes a bioabsorbable material and a non-bioabsorbable material.

10. A system comprising:
a nasal implant delivery tool, the nasal implant delivery tool including:
a handle,
a needle extending distally from the handle, the needle having a needle lumen with a non-circular cross-section having a major axis and a minor axis and a sharp distal end, and
an actuator configured to move a nasal implant along the needle lumen and out of an opening at the sharp distal end of the needle; and
a nasal implant disposed in the needle lumen and including first and second arms at a distal end of the nasal implant, the first and second arms each having a proximal end fixed to the nasal implant and a distal end not fixed to the nasal implant, wherein the distal end of each of the first and second arms is biased to move away from a central longitudinal axis of the nasal implant from a delivery configuration within the needle lumen toward a deployed configuration outside of the needle lumen,
wherein the first and second arms each comprise a beveled surface engaged with an inner surface of the needle lumen on opposite ends of the major axis.

11. A system comprising:
a nasal implant delivery tool, the nasal implant delivery tool including:
a handle,
a needle extending distally from the handle, the needle having a needle lumen with a non-circular cross-section having a major axis and a minor axis and a sharp distal end, and
an actuator configured to move a nasal implant along the needle lumen and out of an opening at the sharp distal end of the needle; and
a nasal implant disposed in the needle lumen and including first and second arms at a distal end of the nasal implant, the first and second arms each having a proximal end fixed to the nasal implant and a distal end not fixed to the nasal implant, wherein the distal end of each of the first and second arms is biased to move away from a central longitudinal axis of the nasal implant from a delivery configuration within the needle lumen toward a deployed configuration outside of the needle lumen,
wherein the nasal implant further includes:
(i) a strain relief section at a proximal end of the nasal implant, and
(ii) a central portion disposed between the proximal end of the nasal implant and the distal end of the nasal implant, the central portion having a flexural rigidity of 50-130 N-mm2.

12. The system of claim 11, further comprising an implant loading chamber communicating with the needle lumen and configured to load the nasal implant into the needle lumen.

13. The system of claim 12, wherein the implant loading chamber is configured to move the nasal implant from the deployed configuration to the delivery configuration as the nasal implant is advanced into the needle lumen.

14. The system of claim 11, further comprising an actuator register configured to indicate a position of the actuator at which the nasal implant is at the distal end of the needle lumen.

15. The system of claim 14, the actuator register comprises one or more markings on the actuator or on the handle.

16. The system of claim 11, further comprising an actuator register configured to indicate a position of the actuator at which at least a distal portion of the nasal implant has been moved out of the needle lumen.

17. The system of claim 16, wherein the actuator register is a stop element preventing further movement of the actuator.

18. The system of claim 11, wherein the nasal implant delivery tool further includes an indicator configured to provide a signal that the nasal implant has been moved out the needle lumen.

19. The system of claim 11, wherein the first and second arms of the nasal implant each include a bevel on a radially inward surface of the distal end.

20. The system of claim 11, wherein the nasal implant includes a bioabsorbable material and a non-bioabsorbable material.

* * * * *